United States Patent
Zocchi et al.

(10) Patent No.: US 8,460,870 B2
(45) Date of Patent: *Jun. 11, 2013

(54) ALLOSTERIC CONTROL OF PROTEINS BY MANIPULATING MECHANICAL TENSION

(75) Inventors: Giovanni Zocchi, Los Angeles, CA (US); Brian Choi, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/187,351

(22) Filed: Jul. 20, 2011

(65) Prior Publication Data

US 2011/0275057 A1    Nov. 10, 2011

Related U.S. Application Data

(63) Continuation of application No. 11/814,275, filed as application No. PCT/US2006/002090 on Jan. 20, 2006, now Pat. No. 8,008,053.

(60) Provisional application No. 60/645,384, filed on Jan. 20, 2005.

(51) Int. Cl.

| | |
|---|---|
| *C12Q 1/68* | (2006.01) |
| *C12Q 1/48* | (2006.01) |
| *C12P 21/00* | (2006.01) |
| *C12N 9/00* | (2006.01) |
| *C12N 9/12* | (2006.01) |
| *C07K 2/00* | (2006.01) |
| *C07K 1/00* | (2006.01) |
| *C07H 21/00* | (2006.01) |

(52) U.S. Cl.
USPC ............ 435/6.1; 435/183; 435/194; 435/69.1; 435/15; 530/402; 530/350; 536/23.1

(58) Field of Classification Search
USPC ...... 435/6, 69.7, 183; 530/402, 350; 536/23.1
See application file for complete search history.

(56) References Cited

PUBLICATIONS

Choi, Brian, et al., "Artificial Allosteric Control of Maltose Binding Protein" Annual Mtg. of the Amer. Phys. Soc., Mar. 22-26, 2004, Canada, Abstract.
Choi, Brian, et al., "Artificial Allosteric Control of Maltose Binding Protein", Phys. Review Letters, Jan. 28, 2005, 94(3):38103.
Choi, Brian, "Allosteric Control Through Mechanical Tension", Phys. Review Letters, Aug. 12, 2005, 95(7):78102.
Kramer, Richard, "Spanning Binding Sites on Allosteric Proteins with Polymer-Linked Ligand Dimers", Nature, Oct. 15, 1998, (London) 395(6703):710-713.
Zocchi, Giovani, "Artificial Allosteric Control of Maltose-Binding Protein", APACS, v228, Part 2, Aug. 2004, pp. U290.
Branden, Carl, et al., Introduction to Protein Structure, Garland Publishing Inc., New York, p. 247, 1991.
Seffernick, Jennifer L., et al., "Melamine Deaminase and Atrazine Chlorohydrolase: 98 Percent Identical but Functionally Different", J. Bacteriol. 183(8):2405-2410, 2001.
Saghatelian, Alan, et al., DNA Detection and Signal Amplification via an Engineered Allosteric Enzyme, J. Am. Chem. Soc. 125(2):344-345, 2003.
Witkowski, Andrzej, et al., "Conversion of a β-Ketoacyl Synthase to a Malonyl Decaroxylase by Replacement of the Active-Site Cysteine with Glutamine", Biochemistry 38: 11643-11650, 1999.

*Primary Examiner* — Delia Ramirez
(74) *Attorney, Agent, or Firm* — Karen S. Canady; candy + lortz LLP

(57) ABSTRACT

A method of altering the conformation of a polypeptide having a known three-dimensional structure is described. The method comprises attaching a first end of a polymer to a first portion of the polypeptide, attaching a second end of the polymer to a second portion of the polypeptide, and altering the mechanical tension of the polymer, thereby altering the conformation of the polypeptide. The alteration of the conformation of the polypeptide may increase or decrease the binding affinity of the polypeptide for a substrate bound by the polypeptide, or alter the catalytic rate of an enzyme. Typically, the polymer is a polynucleotide or polypeptide.

17 Claims, 21 Drawing Sheets

FIG. 18A
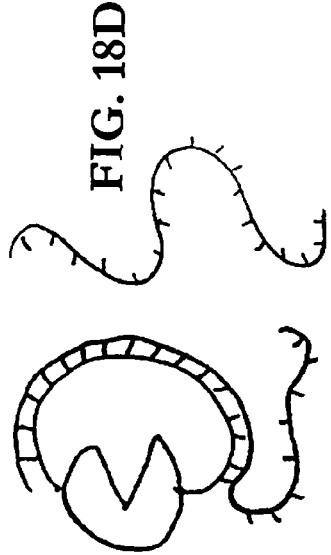
FIG. 18B
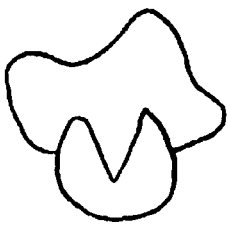
FIG. 18C
FIG. 18D
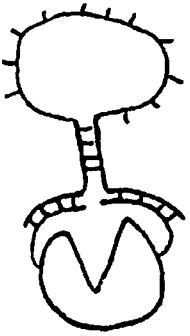
FIG. 18E

SEQUENCE LISTING

<160> NUMBER OF SEQ ID NOS: 10

<210> SEQ ID NO 1
<211> LENGTH: 60
<212> TYPE: DNA
<213> ORGANISM: Artificial Sequence
<220> FEATURE:
<223> OTHER INFORMATION: Synthetic Oligomer

<400> SEQUENCE: 1
ggctcccgat gcggtcagac ctgctctgca ctccccagta cgtgcgggct gtcactcggt    60

<210> SEQ ID NO 2
<211> LENGTH: 60
<212> TYPE: DNA
<213> ORGANISM: Artificial Sequence
<220> FEATURE:
<223> OTHER INFORMATION: Synthetic Oligomer

<400> SEQUENCE: 2
aaataaacaa ataaataaat aaacggggag tgcagattta gtttaaataa agaaatcaaa    60

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 3
tactggggag tgcagagcag                                                20

<210> SEQ ID NO 4
<211> LENGTH: 30
<212> TYPE: DNA
<213> ORGANISM: Artificial Sequence
<220> FEATURE:
<223> OTHER INFORMATION: Synthetic Oligomer

<400> SEQUENCE: 4
gcacgtactg gggagtgcag agcaggtctg                                     30

<210> SEQ ID NO 5
<211> LENGTH: 40
<212> TYPE: DNA
<213> ORGANISM: Artificial Sequence
<220> FEATURE:
<223> OTHER INFORMATION: Synthetic Oligomer

<400> SEQUENCE: 5
agcccgcacg tactggggag tgcagagcag gtctgaccgc                          40

<210> SEQ ID NO 6
<211> LENGTH: 50
<212> TYPE: DNA
<213> ORGANISM: Artificial Sequence
<220> FEATURE:
<223> OTHER INFORMATION: Synthetic Oligomer

<400> SEQUENCE: 6
gtgacagccc gcacgtactg gggagtgcag agcaggtctg accgcatcgg                50

<210> SEQ ID NO 7
<211> LENGTH: 60
<212> TYPE: DNA

-continued

```
<213> ORGANISM: Artificial Sequence
<220> FEATURE:
<223> OTHER INFORMATION: Synthetic Oligomer

<400> SEQUENCE: 7
accgagtgac agcccgcacg tactggggag tgcagagcag gtctgaccgc atcgggagcc        60

<210> SEQ ID NO 8
<211> LENGTH: 41
<212> TYPE: DNA
<213> ORGANISM: Artificial Sequence
<220> FEATURE:
<223> OTHER INFORMATION: Synthetic Primer

<400> SEQUENCE: 8
ccatatggct gtgagcgtcg gcgagggacc ggacaccaag c                            41

<210> SEQ ID NO 9
<211> LENGTH: 41
<212> TYPE: DNA
<213> ORGANISM: Artificial Sequence
<220> FEATURE:
<223> OTHER INFORMATION: Synthetic Primer

<400> SEQUENCE: 9
aagcttacct cgtggtacac ccggggagcc cggtgccgtt c                            41

<210> SEQ ID NO 10
<211> LENGTH: 60
<212> TYPE: DNA
<213> ORGANISM: Artificial Sequence
<220> FEATURE:
<223> OTHER INFORMATION: Synthetic Oligomer

<400> SEQUENCE: 10
ggctcccgat gcggtcagac ctgctctgca ctccccagta cgtgcgggct gtcactcggt        60
```

ALLOSTERIC CONTROL OF PROTEINS BY MANIPULATING MECHANICAL TENSION

This application is a continuation of U.S. application Ser. No. 11/814,275 filed on Jul. 18, 2007, now U.S. Pat. No. 8,008,053, issued Aug. 30, 2011, which is a United States national stage application of PCT/US2006/002090 filed on Jan. 20, 2006, which claims the benefit of U.S. provisional patent application No. 60/645,384, filed on Jan. 20, 2005, the entire contents of which are incorporated herein by reference.

STATEMENT REGARDING FEDERALLY SPONSORED RESEARCH

This invention was made with Government support under Grant Nos. 0405632 and 1006162 awarded by the National Science Foundation, and under Grant Nos. H94003-06-2-0607 and H94003-07-2-0702 awarded by the U.S. Department of Defense/Defense Microelectronics Activity. The Government has certain rights in this invention.

FIELD OF THE INVENTION

The present invention relates to methods and materials relating to the control of protein conformation and function.

BACKGROUND OF THE INVENTION

Allosteric control is the mechanism whereby a control molecule binds to a site on a protein, inducing a conformational change at a distant site, which affects the function of the protein. It is a fundamental molecular control mechanism in the cell: enzymes are typically allosterically controlled (e.g. hexokinase); gene expression is regulated locally by allosteric control of repressors (e.g. the Tryptophan repressor), and non-locally through looping induced by DNA-binding proteins. The latter is a simple example of how binding at one site can effectively modify the chemistry at a distant site: the essence of allosteric control.

An allosterically controlled enzyme is a chemical amplifier: it takes one molecule to switch the enzyme on, but many molecules are synthesized as products of the catalytic reaction. Building artificial molecular devices with similar "chemical transistor" properties has evident scientific and technological interest by creating amplified molecular probes.

SUMMARY OF THE INVENTION

The disclosure provided herein describes the allosteric control of proteins based on mechanical tension. When substrate binding is accompanied by a significant change of conformation of the protein, a mechanical tension favoring one or the other conformation will alter the binding affinity for the substrate. As disclosed herein, we have constructed a chimera where the two lobes of the maltose binding protein (MBP) are covalently coupled to the ends of a DNA oligomer. The mechanical tension on the MBP protein is then controlled externally by exploiting the difference in stiffness between single stranded (ss) and double stranded (ds) DNA. We report that the binding affinity of the protein for its substrates is significantly altered by the tension. Also described herein is the use of this strategy in the manipulation of binding of guanylate kinase to ATP and GMP, as well as the more complex activation of a multimer.

As described in detail below, if the function of a protein is coupled to a change in conformation, there is the possibility of affecting the function through mechanical forces which favor one or the other conformation. In this context we have built an allosteric control module into a protein, by creating a chimera where a DNA oligomer coupled to the protein exerts a mechanical tension on it. The tension on the protein can be varied externally by changing the stiffness of the DNA component of the chimera, through hybridization with different sequences; this changes the binding affinity of the protein for its substrates.

The invention provides a method of altering the conformation of a polypeptide having a known three-dimensional structure. The method comprises attaching a first end of a polymer to a first portion of the polypeptide, attaching a second end of the polymer to a second portion of the polypeptide, and altering the mechanical tension of the polymer. This alteration of the mechanical tension exerted by the polymer on the polypeptide alters the conformation of the polypeptide.

In one embodiment, the polymer is a single stranded polynucleotide. Examples of polynucleotides include DNA, PNA and RNA. Typically, the mechanical tension of the polynucleotide is altered by hybridizing the single stranded polynucleotide to a complementary polynucleotide sequence. In one embodiment, the polynucleotide is from about 10 to about 100 bases in length. The polynucleotide can be from about 20 to about 80 bases in length, such as about 40, 50, 60 or 70 bases in length.

In another embodiment, the polymer is a second polypeptide. The second polypeptide that serves as the polymer can be one that binds a target molecule. Binding to the target molecule thereby effect alteration of the conformation of the polypeptide. The target molecule can be selected either for convenience, as a molecule readily available in the milieu in which the method is practiced, or for the purpose of using the method to detect the presence of the target molecule in the milieu.

In one embodiment, the alteration of the conformation of the polypeptide lowers the binding affinity of the polypeptide for a substrate bound by the polypeptide. In an alternative embodiment, the alteration of the conformation of the polypeptide increases the binding affinity of the polypeptide for a substrate bound by the polypeptide. In some embodiments, the alteration of the mechanical tension of the polypeptide is reversibly controlled by varying access of the polypeptide to an agent or target molecule that binds the polymer.

The invention further provides a composition comprising a polypeptide coupled to a synthetic polymer. The polymer is selected so that, upon contact with a chemical signal, the polymer exerts an alteration of mechanical tension on the polypeptide of about 1 to about 10 pN. The alteration of mechanical tension on the polypeptide effects an alteration of the binding affinity and/or catalytic rate of the polypeptide. In one embodiment, the chemical signal is a molecule that binds the polypeptide. One example of a polypeptide is an enzyme. The alteration of the mechanical tension on the enzyme effects an alteration of the catalytic rate of the enzyme. In some embodiments, the alteration of the binding affinity and/or catalytic rate effects production of a detectable signal. Examples of a detectable signal include, but are not limited to, signals mediated by a fluorescent agent, a chemiluminescent agent or a chromophore.

The invention additionally provides a method of detecting the presence of a target molecule in a sample. The method comprises contacting the sample with a composition of the invention, wherein the target molecule is the chemical signal. The method further comprises detecting the presence of the detectable signal. Presence of the detectable signal is indicative of the presence of the target molecule. Use of this method provides amplified molecular probes for use in detection of specific DNA or RNA or other molecules of interest. The method can be carried out in solution or using surface-bound probes. By amplifying at the assay level, pre-assay amplification of sequences via PCR may be obviated.

The method can be performed in vitro or in situ. Selecting a polymer that interacts with a target molecule can be used to deliver and/or activate the polypeptide that will be allosterically altered in a desired location, such as a cell to be identified, screened for a particular activity or treated. This method allows for targeted delivery of a therapeutic agent that is controlled by allosteric regulation of the polypeptide conformation. In such a case, the polypeptide's function is regulated by manipulating the mechanical tension exerted by the polymer, thereby effecting a therapeutic action.

BRIEF DESCRIPTION OF THE FIGURES

FIG. 10. Sample A shows a 2-fold effect, which rises to a 4-fold effect (sample B) upon purification on a sulfhydryl column, which retains molecules with unreacted Cys.

FIG. 11. The 4-fold decrease in enzymatic activity going from ss to ds chimera, is reversed after adding DNAse, which degrades the DNA of the chimera, releasing the tension. The columns ss_DNAse and ss_$Ca^{2+}$ are controls.

15a. In the holoenzyme complex (R+C subunits, in the absence of cAMP), the αA:A and αC:A helices of the R subunit (arrows) are aligned in close proximity and nearly parallel.

15b. The RIα isomer of the regulatory subunit with cAMP bound shows a large relative displacement of the two alpha helices of interest, αA:A and αC:A, with respect to the structure in 15a. Arrows indicate the spring attachment sites.

Figure 16:
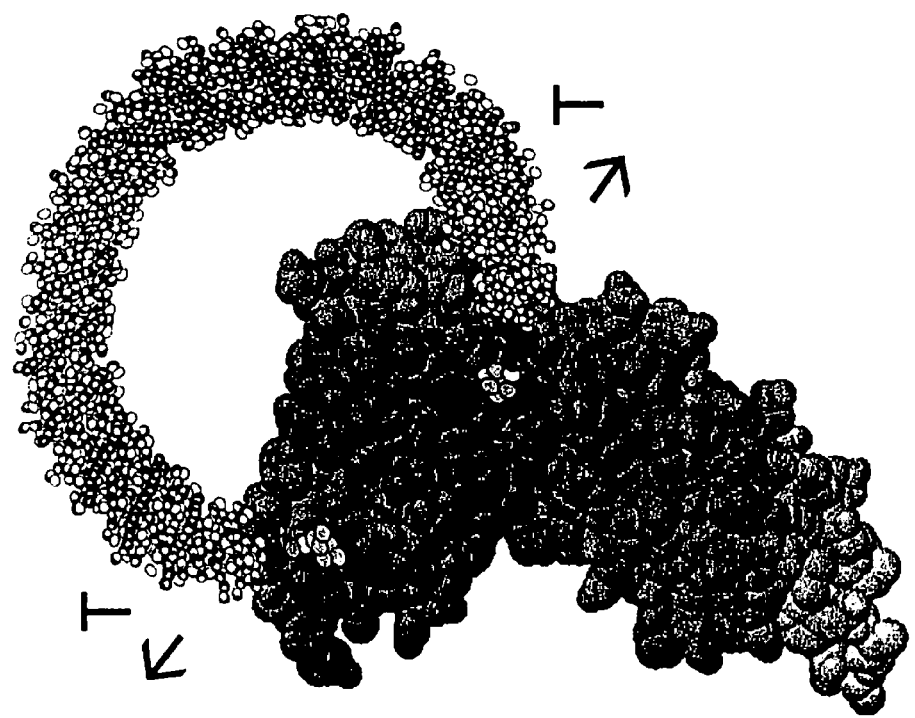

FIG. 16. After hybridization with a complementary strand, the DNA "molecular spring" is much stiffer. It has to bend because of the constraint of the fixed end points, so it exerts a force on the attachment points on the protein's surface, directed along the line joining the attachment points and tending to pull them apart (similarly to a strung bow which pulls on its string).

Figure 17A:
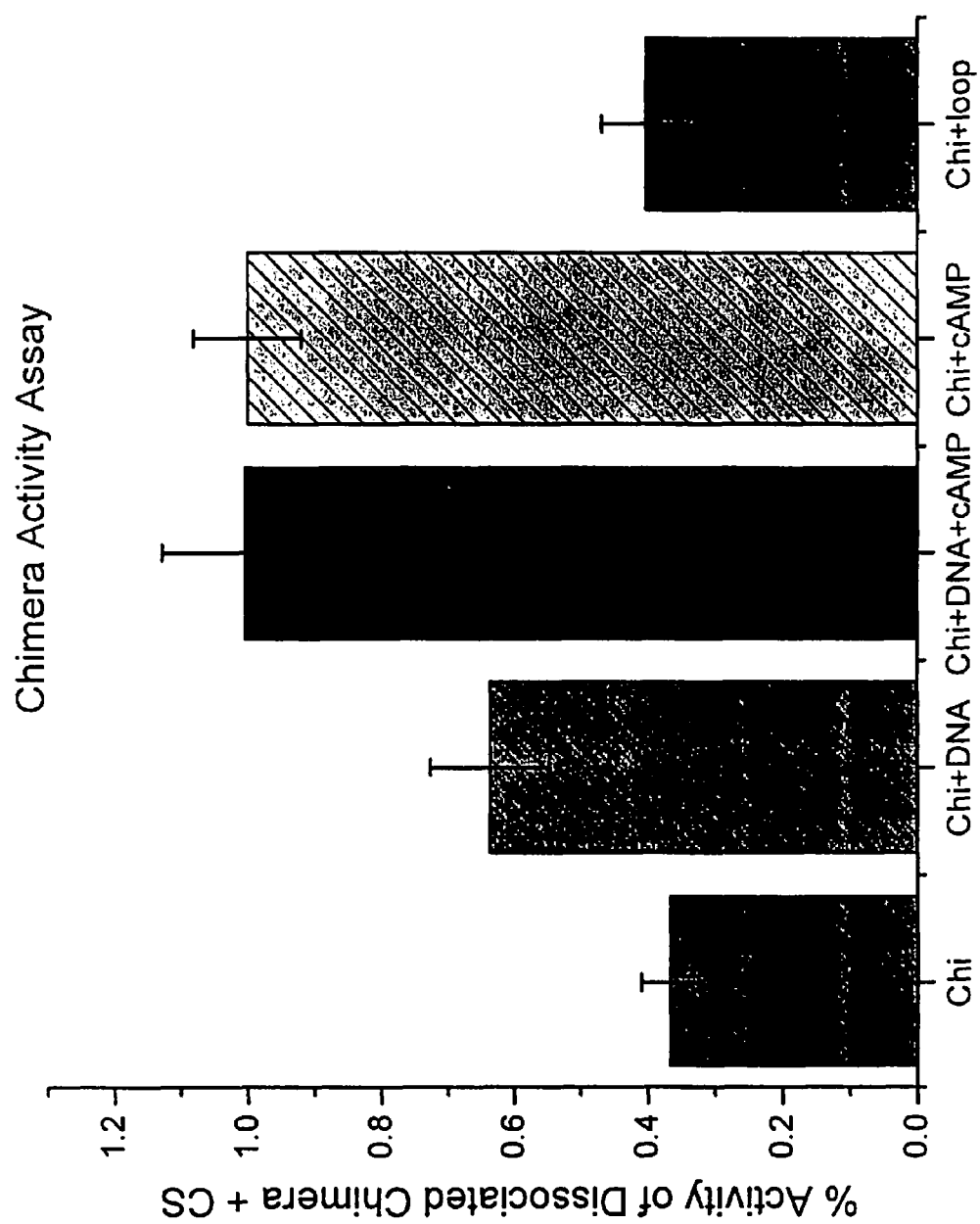
Figure 17B:
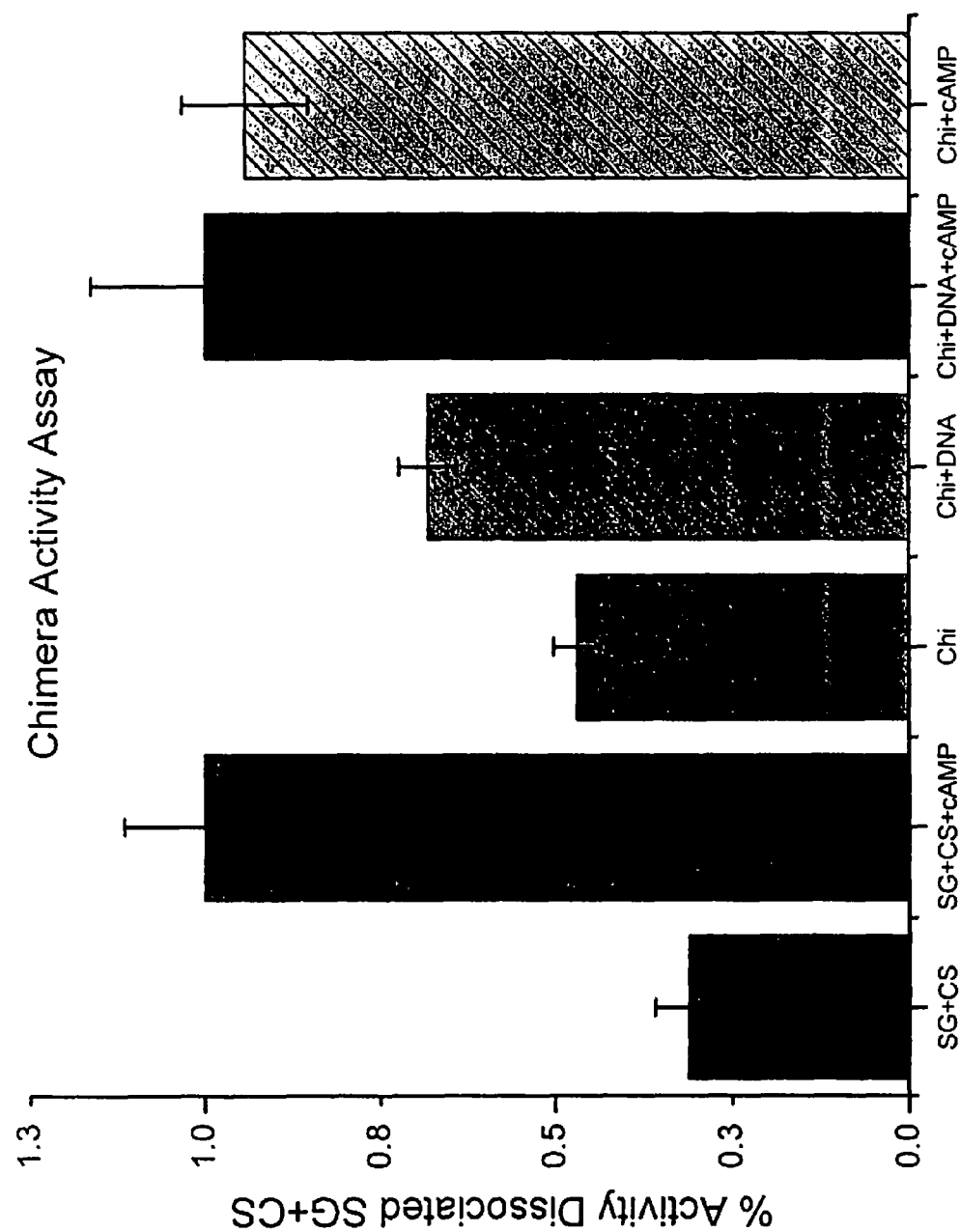

FIG. 17a-17b. Experimental results for the activation of the PKA chimera by mechanical tension (through hybridization of a complementary DNA strand), compared to activation by cAMP. We plot in these bar graphs, for the different samples, a relative measure of kinase activity (A) based on the rate of ATP disappearance, with the activity in the presence of cAMP normalized to 1. The samples are: Chi: ss chimera; Chi+DNA: ss chimera in the presence of the complementary DNA (forming the ds chimera); Chi+cAMP: ss chimera in the presence of cAMP; Chi+DNA+cAMP: ss chimera in the presence of the complementary DNA and cAMP; Chi+loop: ss chimera in the presence of a partially complementary DNA, which binds to the DNA of the chimera but does not produce mechanical tension (this is a control). The data are the average of 5-6 experiments; the error bars are ±1 standard deviation (SD).

17a. By DNA hybridization (mechanical tension), PKA activity increased by a factor 2; with cAMP, by a factor 3. We believe this merely reflects the finite yield of correctly constructed chimeras in the samples. The effects of mechanical tension and cAMP are non-cumulative, since A(Chi+DNA+cAMP)=A(Chi+cAMP). The control Chi+loop supports the picture that the activation effect of the complementary DNA is due to mechanical tension.

17b. For this second, independent synthesis batch (which in general will have a somewhat different yield of correct chimeras), kinase activity increased by 50% with mechanical tension and by a factor 2 with cAMP. CS refers to the holoenzyme constructed with the Cys mutant but with no DNA coupled. We see that the cAMP activation (the dynamic range) is somewhat larger for the mutant (3-fold difference) than for the chimera (2-fold difference). In this plot, both A(Chi+cAMP) and A(CS+cAMP) are normalized to 1.

FIG. 18a-18e. Some alternative configurations for a DNA (or other polymer) based allosteric control module.

FIG. 18a. Upon hybridization, the chimera is mechanically stressed favoring the "open" conformation.

FIG. 18b. The chimera is built with two separate oligomers (sequences a and b); upon hybridization with an ab complementary the two oligomers are pulled towards each other, forcing the protein into the "closed" state.

FIG. 18c. A DNA hairpin is used to force the protein into the closed state; hybridization with a strand complementary to the hairpin loop opens the hairpin, releasing the tension.

FIG. 18d. The chimera is held in the open state; introducing a competitor DNA (complementary to one or the other strands of the chimera) releases the tension, allowing the chimera to close upon binding the substrate.

FIG. 18e. The mechanical tension is provided by a polypeptide chain instead of a DNA oligomer.

DETAILED DESCRIPTION OF THE INVENTION

The invention provides an artificial allosteric control module that can be built into a protein or polypeptide. The principle is to use mechanical tension to influence the conformation of the protein. The tension is derived from the elasticity of another polymer coupled to the protein. Using three different examples of a protein—DNA chimera, we show that the tension can be controlled externally, in this case by a DNA sequence that is allowed to hybridize to the chimera. Based on the elastic properties of DNA, we estimate that we can obtain a significant tension on the protein, up to ~10 pN.

Definitions

All scientific and technical terms used in this application have meanings commonly used in the art unless otherwise specified. As used in this application, the following words or phrases have the meanings specified.

As used herein, "polypeptide" includes proteins, fragments of proteins, and peptides, whether isolated from natural sources, produced by recombinant techniques or chemically synthesized. Polypeptides of the invention typically comprise at least about 6 amino acids.

The term "nucleic acid" or "polynucleotide" refers to a deoxyribonucleotide or ribonucleotide polymer in either single- or double-stranded form (unless indicated as single-stranded form), and unless otherwise limited, encompasses known analogs of natural nucleotides that hybridize to nucleic acids in a manner similar to naturally-occurring nucleotides.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well known conventional methods (see, for example, *Remington's Pharmaceutical Sciences*, 18th edition, A. Gennaro, ed., Mack Publishing Co., Easton, Pa., 1990).

As used herein, "a" or "an" means at least one, unless clearly indicated otherwise.

As used herein, with respect to hybridization conditions, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

Overview

The disclosure provided herein opens a new approach to the control of protein function. It provides a new tool to study the relationship between protein function and conformation, because it allows external control of the conformation. In addition, such control of the catalytic rate of enzymes opens tremendous possibilities for a variety of applications. The disclosure provided herein allows the construction of amplified molecular probes, that can be applied, for example, to the detection of specific DNA sequences. One application of the technology disclosed herein is "smart drugs", which can be turned on or off in the presence of certain transcription products.

The majority of analytical probes are passive (the two important exceptions are ELISA assays and PCR), based for instance on labeling the target molecule to be detected with a fluorescent dye. The immediate purpose of the present invention is to develop a new generation of amplified molecular probes. In addition, the same technology enables the development of "smart drugs".

Amplified probes have enormous advantages over passive probes in terms of sensitivity. Applications which are not feasible with the latter may become feasible with the former. Moreover, new amplification methods have generally resulted in the past in a revolution in technology—witness PCR in molecular biology and the transistor in electronics. The present technology similarly has the potential of revolutionizing the fields of biochemical assays and perhaps drug design. It is based on a general method disclosed herein to build a control module into an enzyme molecule, turning it into a chemical amplifier that can be externally controlled through the presence of a specific molecular species. This gives rise to an amplified probe for that molecular species. In one embodiment, the controlling molecule is a specific DNA sequence, resulting in an amplified DNA hybridization probe. Below we describe proof-of-principle experiments for this embodiment, and also strategies to realize a wider spectrum of amplified probes.

The basis of the technology is the idea of a broadly applicable mechanism of artificial allosteric control for proteins, enzymes in particular. Allosteric control is the mechanism by which a molecule binds to a specific site on a protein, inducing a conformational change at a distant site, which alters the function of the protein. It is the fundamental mechanism of molecular control in the living cell (see, e.g. Alberts, B. et al, "Molecular biology of the cell", Garland Publishing, NY (1994)). The present invention stems from the realization that:

conformational changes in a protein can be driven by mechanical forces such forces can be provided by the elasticity (or more generally the conformational changes) of a second polymer coupled to the protein.

The invention allows one to build modules of allosteric control for proteins based on mechanical tension. The tension is provided by the elasticity, or more generally the conformation, of a polymer coupled to the protein; the conformation or elasticity of the latter is controlled externally by a specific chemical (in a typical example wherein the polymer is a polynucleotide, the complementary DNA). The strength of the method is that it can in principle be applied for the control of almost any protein. This method opens a new field of protein engineering.

Proteins having a structure such as that of maltose binding protein (MBP)—two domains with a binding cleft in between—represent a large classes of proteins: other sugar-binding proteins, kinases, etc. The method described above will apply with little modification to these proteins as well. In general, any protein for which the function is related to a substantial conformational change is susceptible of being controlled by this method. We illustrate in the examples below three representative molecules: MBP, Guanylate Kinase and protein kinase A.

Any protein, regardless of the structure, will unfold under large enough mechanical stress, thus repressing its ability to bind substrates. If the protein refolds upon release of the stress, this process may be reversible. For example, one can control in this way the fluorescence intensity of the Green Fluorescent Protein (GFP), even though this protein may not have a natural functional conformational change.

With DNA as the polymer constituting the allosteric control module, many alternative configurations are possible. In the experiments described above, addition of the complementary strand forced the protein into the "open" state, but the opposite can be realized as well. FIG. 18 gives some examples. Correspondingly, one can design control modules where hybridization will increase the binding affinity for the substrate. In short, the invention provides design modules to turn the protein on and off.

A polymer other than DNA can be used for the control module. In particular, using another polypeptide may be particularly interesting, as it entails the possibility of expressing the chimera in a host cell (e.g. $E.\ coli$ or yeast) and thus avoid or simplify the in vitro synthesis steps. The polypeptide will be such that its conformation is controlled by the molecule to be targeted. Basically this amounts to the novel idea of coupling two proteins in such a way that the conformation of one controls the conformation of the other.

The protein of the chimera can be an enzyme, in particular an enzyme which catalyzes a reaction leading to the production of a fluorescent or chemo-luminescent molecule, or a chromophore. There are many such systems known in the art, some of which are currently used in ELISA assays. The reaction catalyzed by the chimera can also be coupled to further enzymatic reactions to produce readily detectable amplified signals. In summary, in our scheme a chimera built from an enzyme and a control module sensitive to a specific target molecule represents an amplified probe for that target molecule.

The applications of this technology are in principle far-reaching. The invention disclosed herein allows the development of amplified probes to detect specific DNA or RNA sequences, for which the experiments described herein constitute a proof of principle. These amplified probes can revolutionize in vitro and in vivo DNA hybridization assays. They can be used in solution, and also as surface-bound probes in a DNA array format; in both cases, since the amplification happens at the assay level, this could virtually eliminate the need of performing PCR steps prior to the assay. The probes can be injected and survive in live cells, and thereby provide an extraordinary jump in sensitivity for in situ hybridization assays, allowing hybridization studies on single cells.

Similar applications are provided for a virtually unlimited number of biochemical assays, as the disclosed technology is used to develop control modules sensitive to different molecular species (in particular using the protein-polypeptide approach mentioned above). In this scenario, we can develop a set of amplified probes where the enzyme part of the chimera is always the same, while the control module is designed for each target.

In addition, the disclosure allows the construction of "smart drugs" based on this technology. A protein that can be activated by a control module which responds to the presence of a specific DNA or RNA sequence can in principle result in a smart drug, which is administered systemically but is active only locally, within a cell sub-population identified by a specific genetic signature. The protein itself could be the drug—for instance, many forms of cancers depend on hyper—or hypo activity of certain kinases—or it could be the enzyme catalyzing a reaction step leading to the active drug. The protein could be a cytotoxin, such as a bacterial toxin, which would get activated only in the targeted (e.g., cancer) cells, thereby killing the cells.

Therapeutic and Prophylactic Methods

Treatment includes prophylaxis and therapy. Prophylaxis or therapy can be accomplished by a single direct injection at a single time point or multiple time points to a single or multiple sites. Administration can also be nearly simultaneous to multiple sites. Patients or subjects include mammals, such as human, bovine, equine, canine, feline, porcine, and ovine animals. The subject is preferably a human.

A cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors or infected cells with the administration of immune response-modifying agents (such as polypeptides and polynucleotides disclosed herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as CD8+ cytotoxic T lymphocytes and CD4+ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. In a preferred embodiment, dendritic cells are modified in vitro to present the polypeptide, and these modified APCs are administered to the subject. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Administration and Dosage

The compositions are administered in any suitable manner, often with pharmaceutically acceptable carriers. Suitable methods of administering cells in the context of the present invention to a subject are available, and, although more than one route can be used to administer a particular cell composition, a particular route can often provide a more immediate and more effective reaction than another route.

The dose administered to a patient, in the context of the present invention, should be sufficient to effect a beneficial therapeutic response in the patient over time, or to inhibit disease progression. Thus, the composition is administered to a subject in an amount sufficient to elicit an effective immune response to the specific antigens and/or to alleviate, reduce, cure or at least partially arrest symptoms and/or complications from the disease. An amount adequate to accomplish this is defined as a "therapeutically effective dose."

Routes and frequency of administration of the therapeutic compositions disclosed herein, as well as dosage, will vary from individual to individual, and may be readily established using standard techniques. In general, the pharmaceutical compositions and vaccines may be administered, by injection (e.g., intracutaneous, intratumoral, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. In one embodiment, 2 intradermal injections of the composition are administered 10 days apart.

A suitable dose is an amount of a compound that, when administered as described above, is capable of promoting an anti-tumor immune response, and is at least 10-50% above the basal (i.e., untreated) level. Such response can be monitored, for example, by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to nonvaccinated patients. In general, for pharmaceutical compositions and vaccines comprising one or more polypeptides, the amount of each polypeptide present in a dose ranges from about 100 µg to 5 mg per kg of host. Suitable volumes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a tumor protein generally correlate with an improved clinical outcome. Such immune responses may generally be evaluated using standard proliferation, cytotoxicity or cytokine assays, which may be performed using samples obtained from a patient before and after treatment.

EXAMPLES

The following examples are presented to illustrate the present invention and to assist one of ordinary skill in making and using the same. The examples are not intended in any way to otherwise limit the scope of the invention.

Example 1

Artificial Allosteric Control of Maltose Binding Protein

In this example, we demonstrate the allosteric control of a protein based on mechanical tension. When substrate binding is accompanied by a significant change of conformation of the protein, a mechanical tension favoring one or the other conformation will alter the binding affinity for the substrate. We have constructed a chimera where the two lobes of the maltose binding protein are covalently coupled to the ends of a DNA oligomer. The mechanical tension on the protein is controlled externally by exploiting the difference in stiffness between single stranded and double stranded DNA. We report that the binding affinity of the protein for its substrates is significantly altered by the tension.

Figure 1A:
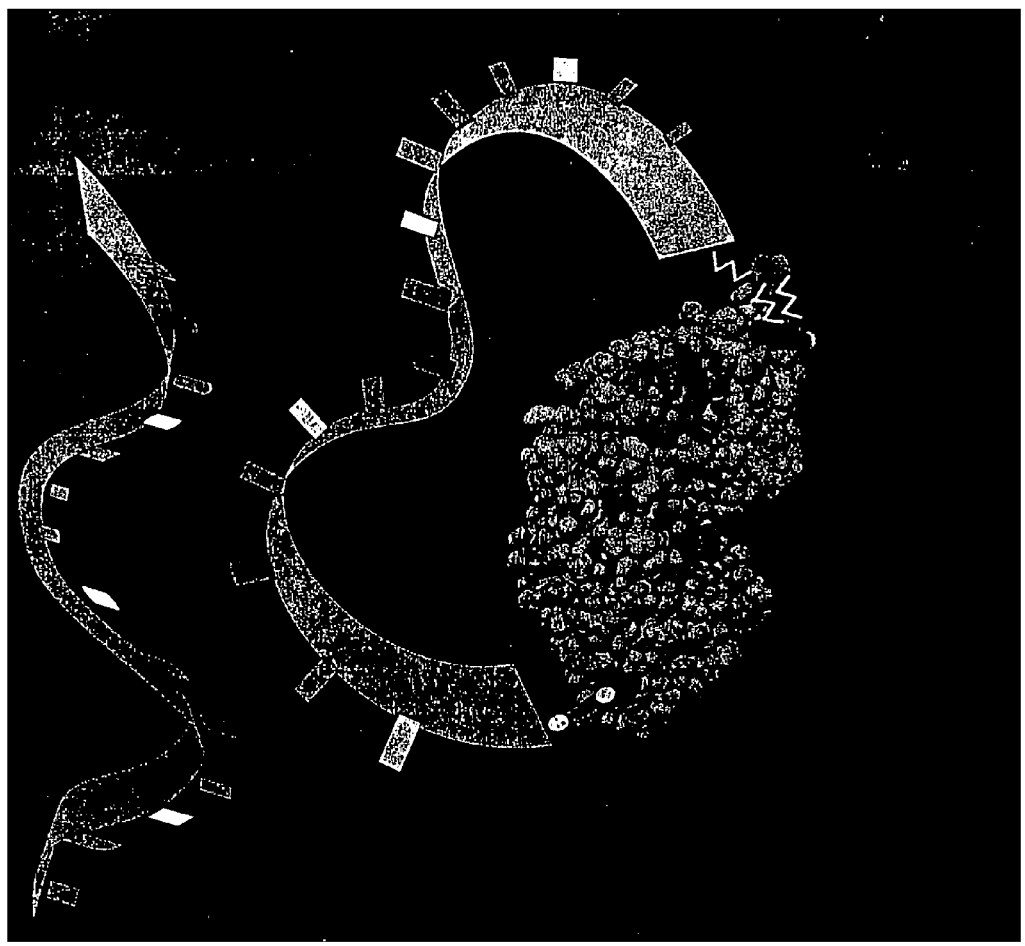
FIG. 1A. The MBP-DNA ss construct. The MBP structure is from the Protein Data Bank. The location of the Lys 202→Cys mutation is shown in red, the location of the His-tag in purple. The distance between these two groups is ~7 nm. The ss DNA 60 mer is flexible and exerts only a small compression on the molecule.

The system described herein utilizes the Maltose-Binding Protein (MBP) of E. coli, the periplasmic component of the maltose transport system. Maltose binds in the cleft between the two lobes of the structure (FIG. 1), inducing a large (~1 nm amplitude) conformational change which brings the two lobes closer together, clamping down on the maltose. This is known from the crystal structure of the bound and unbound forms, and also from EPR spectroscopy. The general idea of the present experiment is to control this conformational change through the mechanical tension derived from the bending elasticity of a second polymer coupled to the protein. For this purpose, MBP was modified by site directed mutagenesis to introduce two "chemical handles" on opposite sides of the two lobes (FIG. 1): Lys 202 was mutated to Cys, and a hexahistidine-tag was appended at the N terminus. These specific binding sites were used to attach a 60 bases long single stranded (ss) DNA oligomer (FIG. 1a) by one end to the Cys residue (through a covalent (disulfide) bond) and by the opposite end to the His-tag (through a metal ion complex). For a second chimera (a Cys double mutant), both sides were covalently attached through disulfide bonds. The functionality of the chimera is intact: the measured binding affinity K for maltose and maltotriose ($K_1$=0.9 $\mu M^{-1}$; $K_2$=5.3 $\mu M^{-1}$) is within the range of literature values for the wild type MBP (0.7-1.1 $\mu M^{-1}$ for maltose, 5-6 $\mu M^{-1}$ for maltotriose).

Figure 1B:
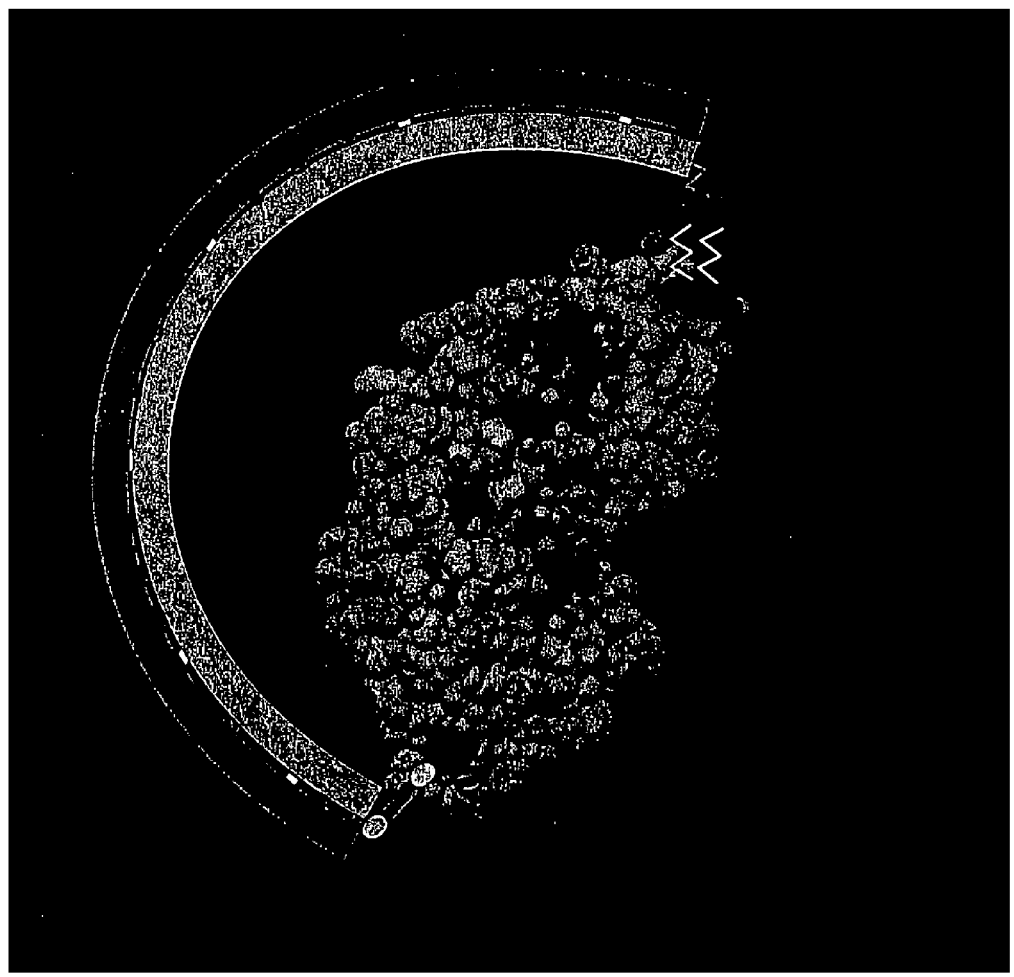
FIG. 1B. After hybridization with a complementary strand, the DNA part of the chimera is more rigid and exerts a mechanical stress on the protein.

The principle of the experiment is as follows. A DNA oligomer with a length intermediate between the persistence length of ss DNA ($l_{ss}$~1 nm or 3 bases) and that of ds DNA ($l_{ss}$~50 nm or 150 bases) is flexible in the ss form, but stiff in the ds form. Thus the 60 mer ss DNA of the chimera (FIG. 1a) does not exert a tension on the protein (actually, it exerts a small entropic compression). However if this DNA strand is hybridized with a complementary, it will exert a mechanical tension on the protein, because the stiff ds DNA molecule has to bend (FIG. 1b). The mechanical equivalent is a strung bow, where the protein is the string and the DNA is the bow. This tension favors the "open" conformation of MBP described above, and therefore lowers the binding affinity for the substrates. We obtained similar results using both malto-triose or maltose as substrate; here we report the former.

Materials and Methods

Mutagenesis & Purification. The MBP encoding DNA was obtained by digesting pMAL-2c (New England BioLabs) with BamHI-NdeI. The DNA was then ligated into pET16b (Novagen). The QuikChange Multi Site-Directed Mutagenesis Kit (Stratagene) was used to introduce the K202C mutation into the MBP gene (and, for the double Cys mutant, the K6C/D207C mutations). The mutagenesis was confirmed by sequencing. The his-tagged MBP mutant was purified using a Superflow Ni-NTA® column (Qiagen). SDS-PAGE of the mutant showed a single, well defined band. The protein was expressed at ~10 mg/L culture/OD (600 nm).

MBP-DNA Complex conjugation. Oligonucleotides and Ni-NTA magnetic beads were from Qiagen. The linker Bis(Carboxymethyl)-L-lysine hydrate (NTA-Lys,), the reductant Tris(2-carboxyethyl)phosphine (TCEP), and the maltose and maltotriose were from Sigma. The 5'-thiol and 3'-amino modified 60 bp DNA oligomer was conjugated to the lysine side of the NTA-Lys linker through glutaraldehyde. The DNA oligomers, at a concentration of 20 $\mu M$, were incubated at room temperature with glutaraldehyde 25% in PBS for 4 hrs, adding NACNBH (a reducing agent) for the last 1 hr, at 4 C. To this solution, after dialysis against PBS, was added NTA-Lys 1 mM, for 5 hrs, and the solution dialyzed in the end.

Figure 5:
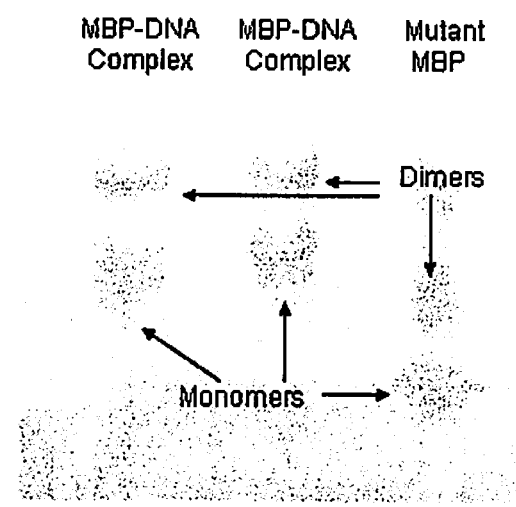
FIG. 5. The native gel (running downwards) shows the reduced mobility of the MBP-DNA construct (lanes 1 & 2) with respect to the MBP mutant (lane 3). Both MBP monomers and dimers are present, as indicated.

The mutant MBP was fixed onto Ni-NTA magnetic agarose beads (beads 5% w/v, total volume 1 mL, 2× excess MBP with respect to the beads' binding capacity). The conjugated DNA oligomers, deprotected using TCEP, were incubated with the beads (final DNA conc. 10 $\mu M$) for 5 days, with the addition of Glutathione. After washing, the MBP-DNA conjugate was eluted from the beads using imidazole. An excess of $Ni^{2+}$ ions were added into the solution; then imidazole was used to specifically release the $Ni^{2+}$ ions from the His-tag; finally imidazole was dialyzed out, completing the linkage of the oligomer to the mutant MBP by the $Ni^{2+}$ complex. The final MBP-DNA complex is shown on a native polyacrylamide gel compared to the MBP mutant in FIG. 5: the lower mobility of the complex is evident from the gel (the MW of MBP is approximately 42.5 kDa, while the MBP-DNA complex is approximately 61 kDa).

Figure 2:
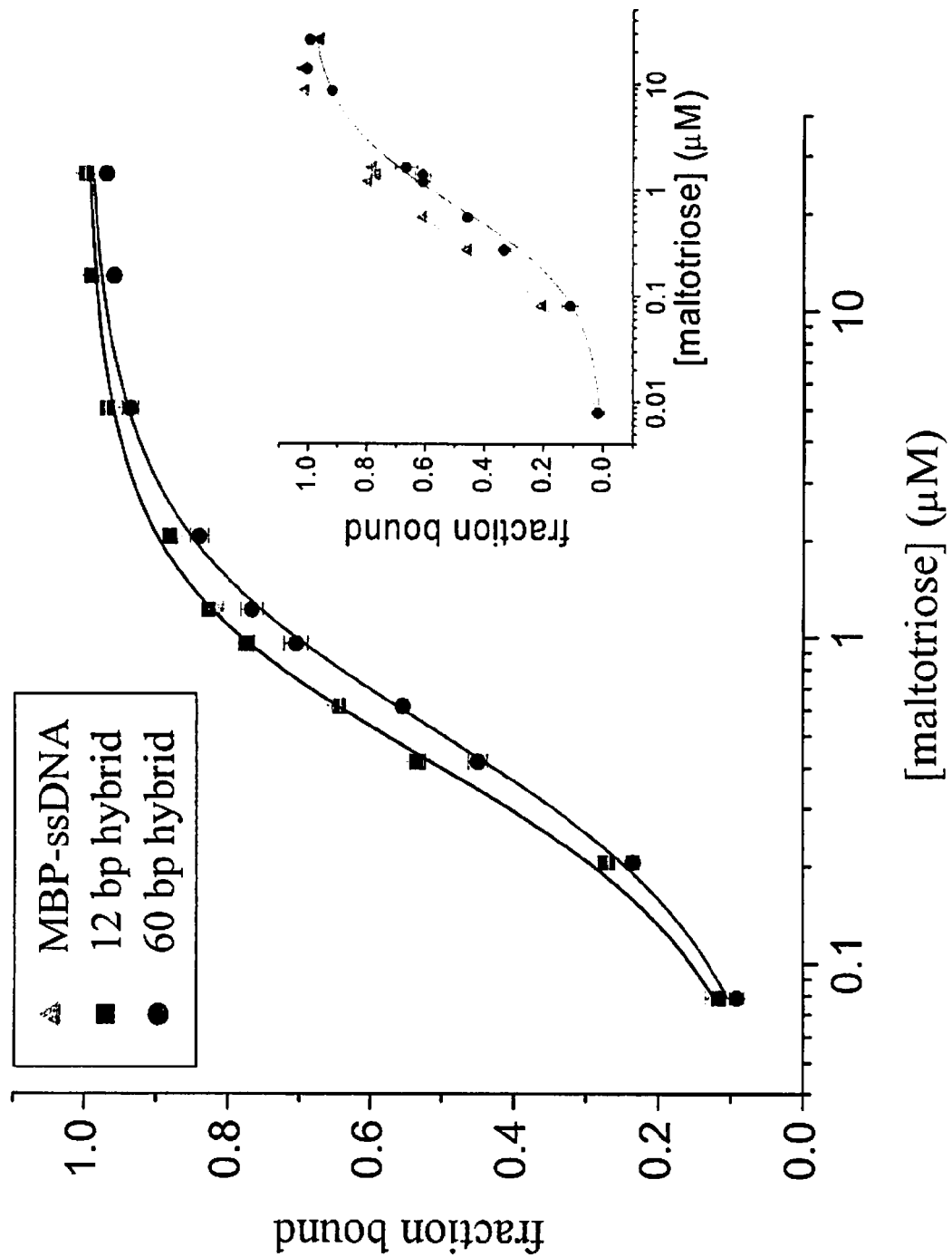
FIG. 2. Titration curves (obtained from the change in Trp fluorescence normalized between 0 and 1) displaying the fraction of proteins with a bound substrate (malto-triose) vs. substrate concentration. Each point is the average of 4-6 different experiments; the error bars are ±1 SD. The lines are fits using eq. (1), from which the binding constants are extracted. The 60 bp hybrid shows a ~35% reduction in binding affinity K with respect to the controls (MBP—ss DNA and 12 bp hybrid). Inset: results for a double Cys chimera where the DNA is coupled covalently on both sides; the 60 bp hybrid now shows a ~60% reduction in K.

The data in the inset of FIG. 2 were obtained with a double Cys mutant (K6C/D207C), using the heterobifunctional linker sulfo-SMCC (Pierce) to couple the DNA covalently on both sides. This DNA was the same 60 mer sequence below, but amino-modified at both ends.

Oligomer sequences. The sequence of the 60 mer used for the construction of the chimera was:

```
                                       (SEQ ID NO: 1)
5'-thiol-GGCTCCCGATGCGGTCAGACCTGCTCTGCACTCCCC AGTACGTGCGGGCTGTCACTCGGT-amino
```

To form the different hybrids, the following oligomers were used:

```
L = 12:
                                       (SEQ ID NO: 2)
5'-AAATAAACAAATAAATAAATAAACGGGGAGTGCAGAT
TTAGTTTAAATAAAGAAATCAAA

L = 20:
                                       (SEQ ID NO: 3)
TACTGGGGAGTGCAGAGCAG

L = 30:
                                       (SEQ ID NO: 4)
GCACGTACTGGGGAGTGCAGAGCAGGTCTG

L = 40:
                                       (SEQ ID NO: 5)
AGCCCGCACGTACTGGGGAGTGCAGAGCAGGTCTGACCGC

L = 50:
                                       (SEQ ID NO: 6)
GTGACAGCCCGCACGTACTGGGGAGTGCAGAGCAGGT
CTGACCGCATCGG

L = 60:
                                       (SEQ ID NO: 7)
ACCGAGTGACAGCCCGCACGTACTGGGGAGTGCAGAGC
AGGTCTGACCGCATCGGGAGCC
```

Mechanical tension. To estimate the tension exerted by the DNA on the protein we use a simple mechanical model (FIG. 4 inset) where the ds portion of the DNA is modeled as a bow of contour length s (20 nm for the 60 bp hybrid), bent into an arc of radius R. The two ss ends of the DNA are modeled as (nonlinear) springs. The chord length x is the sum of the lengths of the springs (2b), plus the distance between the attachment points on the protein (7 nm). To calculate the force needed to bend the bow, we start with the work per unit length required to bend it:

$$\frac{W}{s} = \frac{B}{2R^2} \quad (S1)$$

where s is the contour length of the bow, B the bending modulus, R the radius of curvature. In terms of the chord length x, the force which has to be applied at the ends (the tension F in the string, if this was a bow) is:

$$F = -\frac{\partial W}{\partial x} \quad (S2)$$

(the derivative is taken at fixed s). In terms of s and R:

$$x = 2R\sin\left(\frac{s}{2R}\right) \quad (S3)$$

and one obtains after some algebra:

$$T = \frac{sB}{R^3}\left[2\sin\left(\frac{s}{2R}\right) - \frac{s}{R}\cos\left(\frac{s}{2R}\right)\right]^{-1} \quad (S4)$$

In this purely mechanical approach, there is a threshold force for bending the bow: $T(R \to \infty) = T_0 = 12 B/s^2$. For a polymer such as ds DNA, the bending modulus is related to the persistence length through:

$$\ell \approx \frac{B}{kT} \quad (S5)$$

(Bloomfield, V., Crothers, D., & Tinoco, I. *Nucleic Acids: structures, properties, and functions*, University Science Books, Sausalito, Calif. (2000).)

Since $l_{ds} \approx 50$ nm, $kT \approx 4$ pN×nm, the bending modulus for ds DNA is approximately B≈200 pN×nm².

The extension of the ss DNA "springs" is calculated from the mechanical equilibrium condition that the tension in the springs (FIG. 4 inset) is the same as the force needed to bend the bow. At zero force, the EED of the spring is the Flory radius $b(F=0)=R_F=l_p N_p^{3/5}$ where $l_p \approx 1$ nm (~3 bases) is the persistence length and $N_p=N_{ss}/3$ is the number of persistence lengths ($N_{ss}$ is the number of bases in the ss tail). For a given force F, we obtain the extension of the spring, b, using published data of the force vs. relative extension for ss DNA, from Dessinges, M. N. et al., Phys. Rev. Lett. 89, 248102 (2002), and our own work, Singh-Zocchi, M., et al., Proc. Natl. Acad. Sci. USA 100, 7605-10 (2003). Using the same notation as in those references, α is the extension of the ss DNA relative to the contour length $l_0$ of the corresponding ds DNA, i.e. $b=\alpha l_0$, $l_0=N_{ss}/3$ nm and the chord length in FIG. 4 (inset) is $x=7$ nm+2 b (7 nm being the distance of the attachment points on the protein). From the data in Dessinges et al. (supra), we have the tension F(α) of the ss at relative extension α (in the regime of interest here, α~1, this curve is not approximately linear, in fact it is roughly exponential). Given the number of hybridized bases L (the contour length of the ds part of the DNA is then s=L/3 nm) we determine α, and therefore the tension F, numerically from the condition F(α)=T using eqs. S3 and S4.

Figure 4:
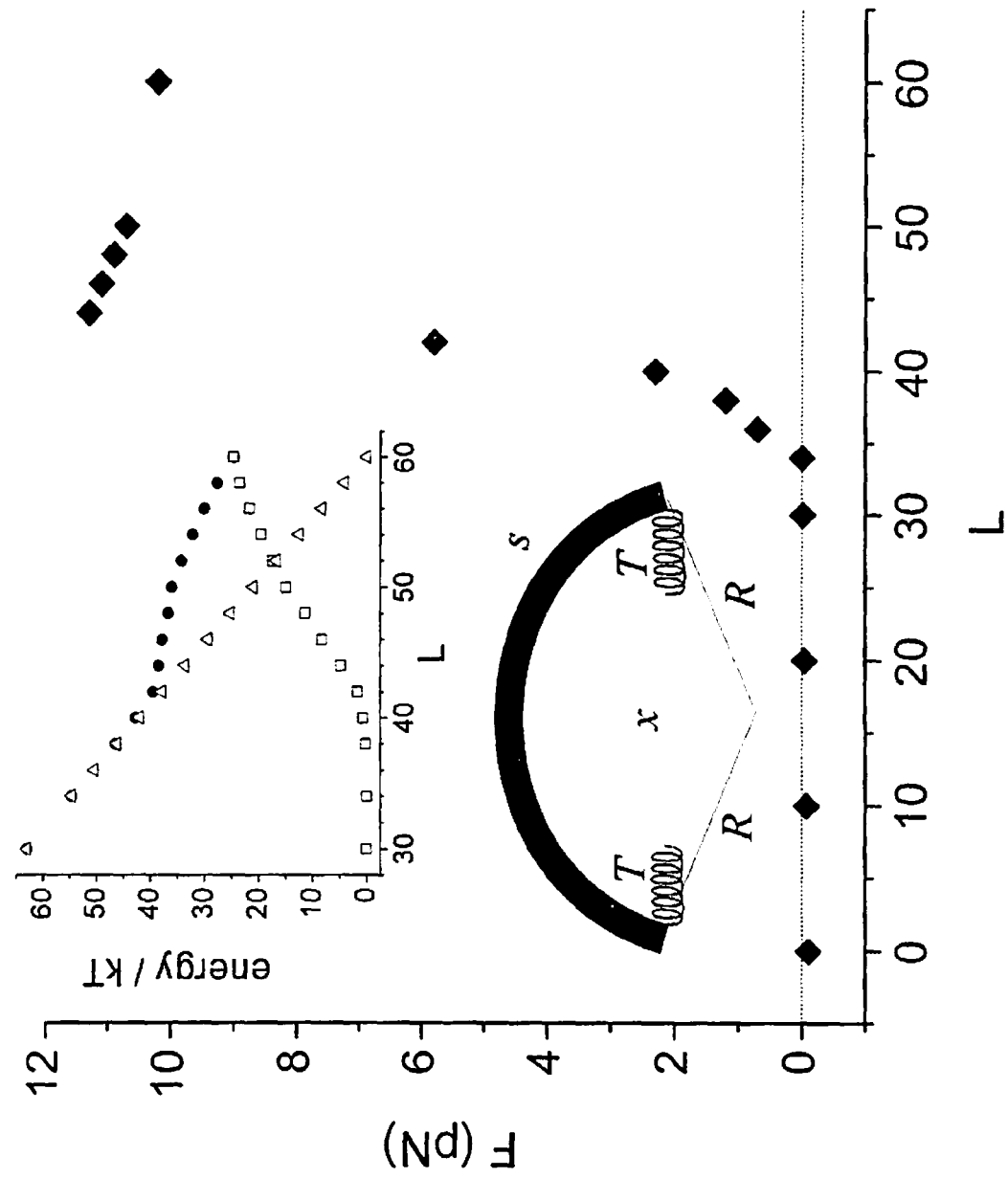
FIG. 4. Mechanical tension F on the protein vs length L of the complementary hybridized to the chimera, as predicted by the mechanical model shown in the inset. Inset: the elastic and bond free energies in the DNA (in units of kT), from the model. Open squares: the total elastic energy $E_{elastic}$ (for details see FIG. 7). Open triangles: the free energy of hybridization $F_{bond} \approx 2.1$ kT per open bp. Filled circles: the total free energy of the system $F_{tot} = E_{elastic} + F_{bond}$.

The result for the mechanical tension vs hybridization length L is shown in FIG. 4. As the number of hybridized bases, L, is reduced from L=60, the slight increase in F between L=60 and L=44 is related, in the model, to the fact that if the arclength of a semi-circular bow is shortened, while the chord is lengthened by the same amount, the tension of the string actually increases. The sharp drop in F between L=44 and L=42 is due to the tension F falling below the threshold for bending the bow in the mechanical model. For L<42 the ds part of the DNA is not bent, and all the elastic energy is in the ss springs. These sharp features are presumably smoother in the real system. At L=34 the force drops to zero, because the extension of the ss springs is then equal to the zero force Flory radius. For L<34 the force goes negative, i.e. there is a small compression on the protein, because the EED of the DNA polymer is forced to be larger than the unperturbed Flory radius $R_F$. This excluded volume effect is relatively weaker than the bending elasticity effects; the corresponding force is calculated approximately (for γ≈1) as $$\text{force} \approx -\frac{kT}{R_F}(\gamma - 1) \quad (S6)$$

where γ is the Flory-DeGennes swelling parameter defined by EED=γ $R_F$. The maximum compression, for L=0, is only: force≈−0.1 pN. However, this is somewhat overestimated because it does not take into account the excluded volume due to the presence of the protein.

Figure 3:
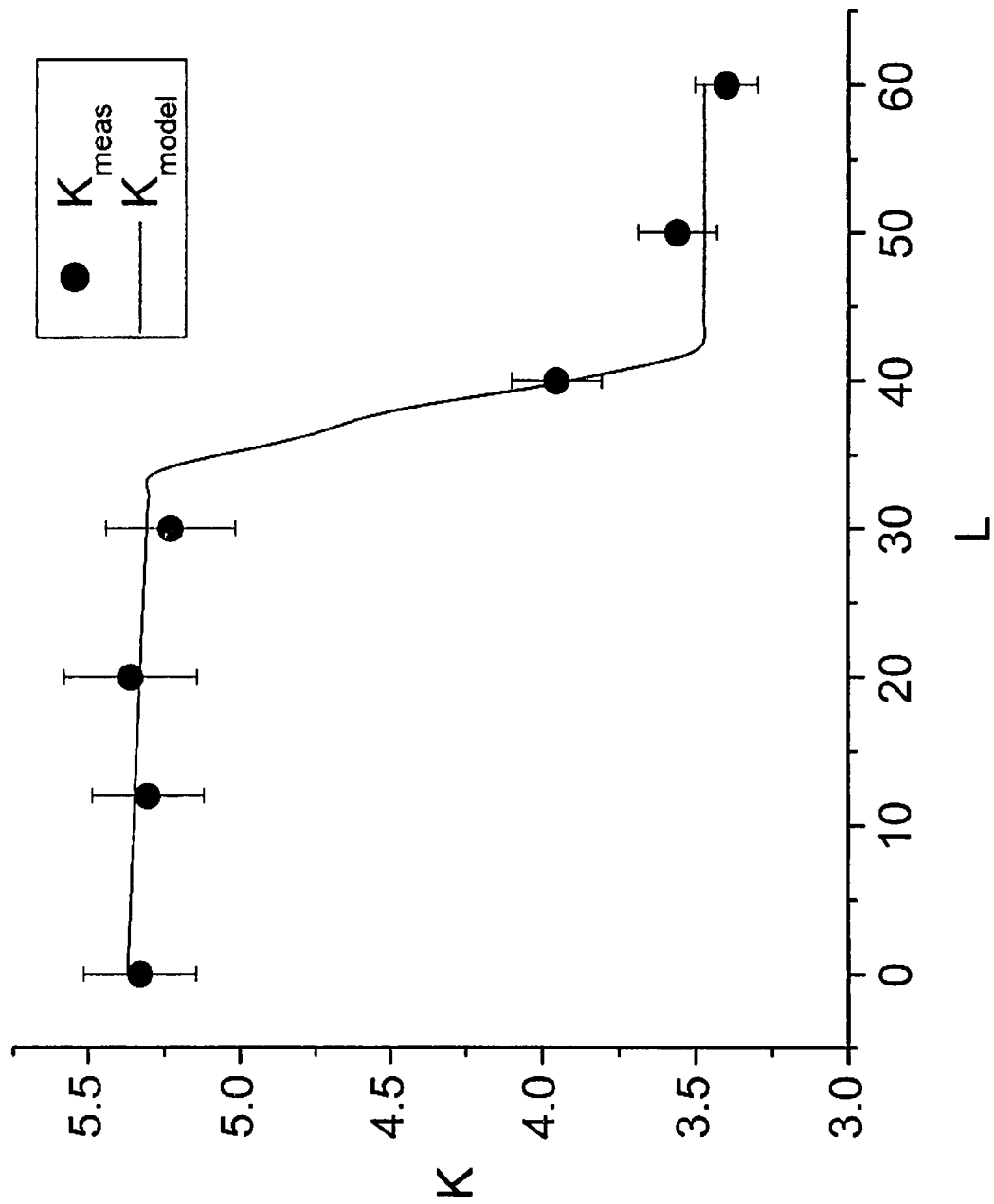
FIG. 3. Binding affinities K (in $\mu M^{-1}$) for malto-triose vs. length of the complementary (L) hybridized to the 60 mer DNA of the chimera. Each point represents the average of 4-6 titration curves; error bars are ±1 SD. The mechanical tension on the protein is expected to set in for L>34 (FIG. 4). The data therefore confirm that the change in K is caused by the mechanical tension. The L=12 data point is an especially significant control, because the length of the complementary strand for this case is actually 60 bases, but only 12 are complementary to the DNA of the chimera, so no tension is expected to develop. The continuous line is the prediction of a simple thermodynamic model (eq. (2)) described in the text.

In conclusion, the qualitative features of FIG. 4, when compared to the measured substrate binding affinities K vs L (FIG. 3), support the conclusion that the change in K is caused by the mechanical tension.

Figure 6:
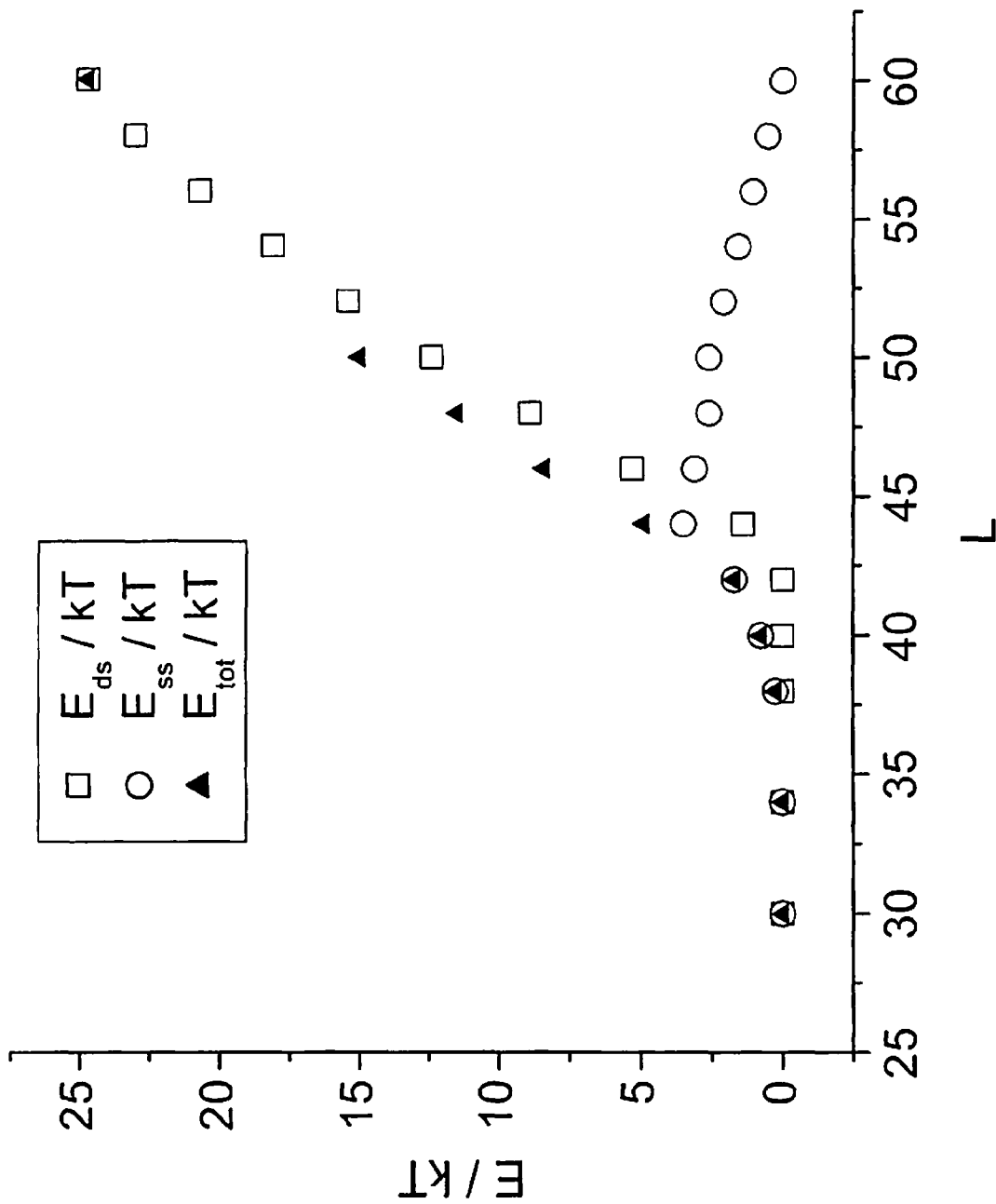
FIG. 6. The elastic energy stored in the DNA, from the model. Energies are in units of kT, L is the length (number of bases) of complementary hybridized to the chimera. Open squares: the bending energy $E_{ds}$ of the ds portion of the DNA. Open circles: elastic energy $E_{ss}$ of the stretched ss ends of the DNA. Filled triangles: the total elastic energy $E_{elastic} = E_{ds} + E_{ss}$.

Energy considerations. In FIG. 6 we show the energetics of the same model. The elastic energy in the ds bow is calculated from (S1):

$$E_{ds} = \frac{sB}{2R^2}$$

where the curvature 1/R is calculated from S3. With the same notation as above for α, $l_0$ and b, the elastic energy in the ss springs is calculated from:

$$E_{ss} = 2l_0 \int_{\alpha=R_F/l_0}^{\alpha=b/l_0} F(\alpha)\,d\alpha \quad (S7)$$

where $R_F=l_p N_p^{3/5}$ is the Flory radius, F(α) is the experimental force-stretch curve in Dessinges, M. N. et al., Phys. Rev. Lett. 89, 248102 (2002), and the factor 2 comes because there are 2 ss springs. The total elastic energy $E_{elastic}=E_{ds}+E_{ss}$ is shown in the figure. In FIG. 4 (inset) we compare this elastic energy with the bond free energy $F_{bond}$ of the partially hybridized 60 mer. The latter is an average obtained using the program MFOLD (Zuker, M., *Nucleic Acids Res.* 31 (13), 3406-15, (2003)), giving for our specific sequence ΔF≈2.1 kT per open bp. The total free energy of the DNA is then $F_{tot}=E_{elastic}+F_{bond}$, and the inset of FIG. 4 shows that the DNA will indeed hybridize, the mechanical constraint notwithstanding, as the minimum of $F_{tot}$ is at L=60. For instance, the free energy difference $\Delta F_{tot}$ between L=60 and L=50 is over 10 kT.

Yield. With a yield p of correct chimeras, it is easily seen that if the low substrate concentration part of the titration curve is used to extract K, then the measured affinity is approximately $K_1 \approx p\ K(F)+(1-p)\ K_{closed}$, while if the high substrate concentration part of the titration curve is used, one extracts $K_2^{-1} \approx p\ K(F)^{-1}+(1-p)\ K_{closed}^{-1}$, so that an approximate interpolation formula for the measured K is: $K_{meas} \approx \frac{1}{2}[p\ K(F)+(1-p)K_{closed}] \pm \frac{1}{2}[p\ K(F)^{-1}+(1-p)K_{closed}^{-1}]^{-1}$. This form was used for the fit of FIG. 3.

Measurement of the MBP-Maltose binding affinity. Fluorescence measurements were performed with a Photon Technology Instruments fluorimeter, in 3 mL cuvettes, at 20±2° C. The excitation and emission wavelengths were $\lambda_{ex}$=281 nm, $\lambda_{em}$=341 nm. The concentration of MBP-DNA chimera was approximately 50 nM in phosphate buffered saline (PBS).

The fraction of proteins with a bound maltose is f=[M]/($K^{-1}$+[M]) where K is the binding constant, M is the maltose, P the protein, and [ ] means equilibrium concentration. In terms of the initial maltose concentration [M]$_o$ the relation is:

$$[P]_0 f^2 - (K^{-1} + [M]_0 + [P]_0) f + [M]_0 = 0 \quad (1)$$

(Stinson, R., and J. HolBrook, *Biochem. J.* 131, 719-28 (1973).)

The binding constant K was determined by fitting the data to eq. (1), after correcting for dilution effects.

Results

Through native gel electrophoresis we confirmed that the samples consist primarily of protein-DNA complexes. For these samples, we measured the binding affinity for maltotriose and maltose, for the chimera, and for the chimera hybridized to DNA of different lengths L. The binding constant K was measured by titration, from the fraction of proteins with a bound substrate f determined by monitoring Trp fluorescence, which is quenched by about 20% upon substrate binding (Szmelcman, S., et al., *Eur. J. Biochem.* 65, 13-19 (1976)). Within a two-state description, the change in fluorescence normalized between 0 and 1 gives the fraction of proteins in the bound (or closed) state, f.

FIG. 2 shows titration curves f vs maltotriose concentration [M] for the ss chimera, and the chimera hybridized to DNA with 12 and 60 base complementarity. For the 60 bp hybrid, the binding affinity for malto-triose is lowered by 35%. The 12 bp hybrid is a control, where no mechanical tension is expected to develop. This complementary DNA is actually 60 bases long, but only 12 are complementary to the DNA of the chimera. It shows that the presence of a second DNA strand attached to the chimera does not by itself change the binding affinity.

Figure 7:
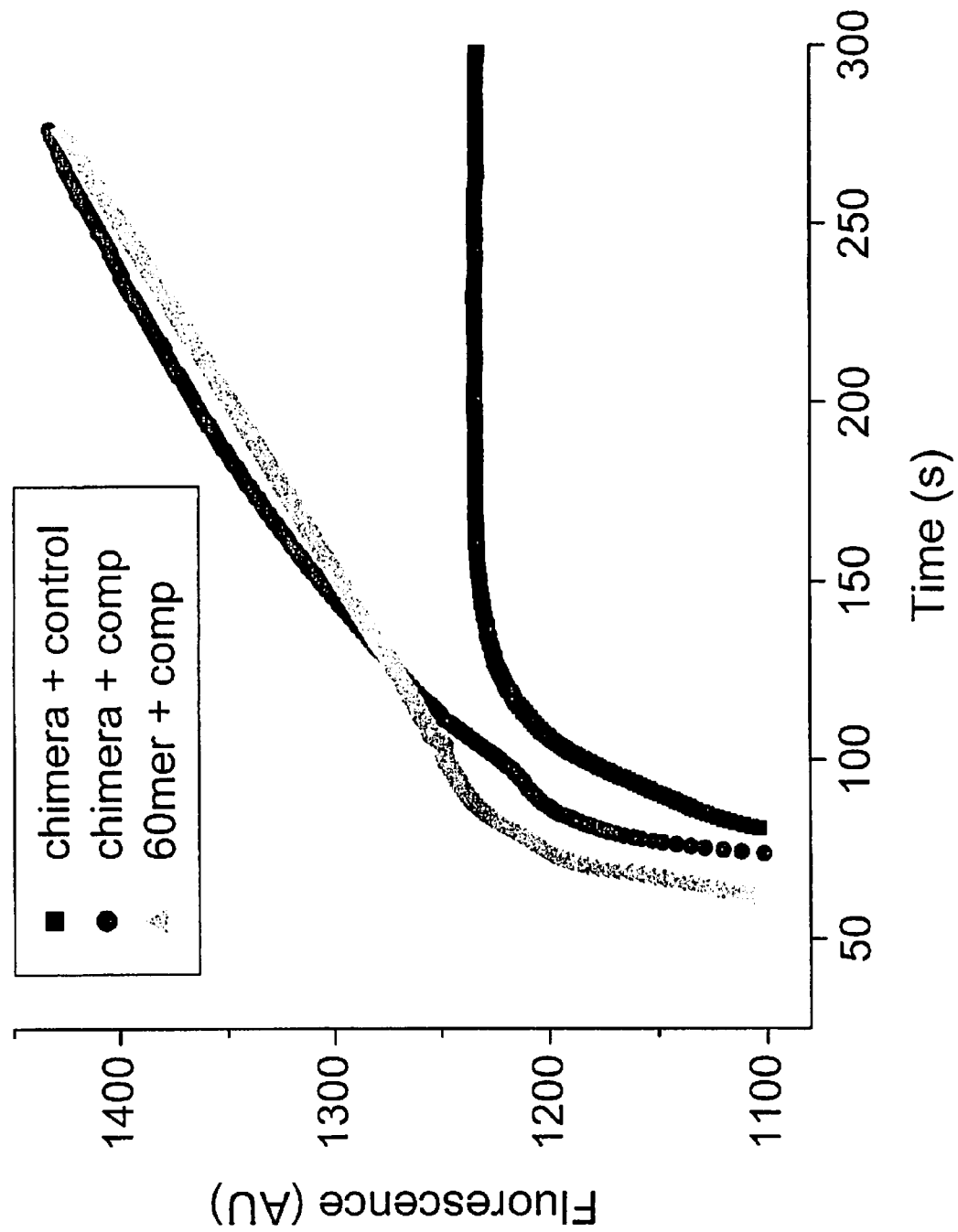
FIG. 7. DNA hybridization curves obtained from the fluorescence intensity due to the fluorescent dye PicoGreen, which binds preferentially ds DNA. Black squares: chimera+control (a non-complementary DNA 60 mer); red circles: chimera+complementary 60 mer; green triangles: the DNA 60 mer used in the construction of the chimera+complementary 60 mer. The initial fast increase in fluorescence is caused by the dye binding to ss DNA, when the latter is added to the solution. The curves have been corrected for bleaching. The black curve (control) shows no hybridization signal, while the red and green curves show similar hybridization signals, indicating that the complementary 60 mer does hybridize to the chimera.
Figure 8:
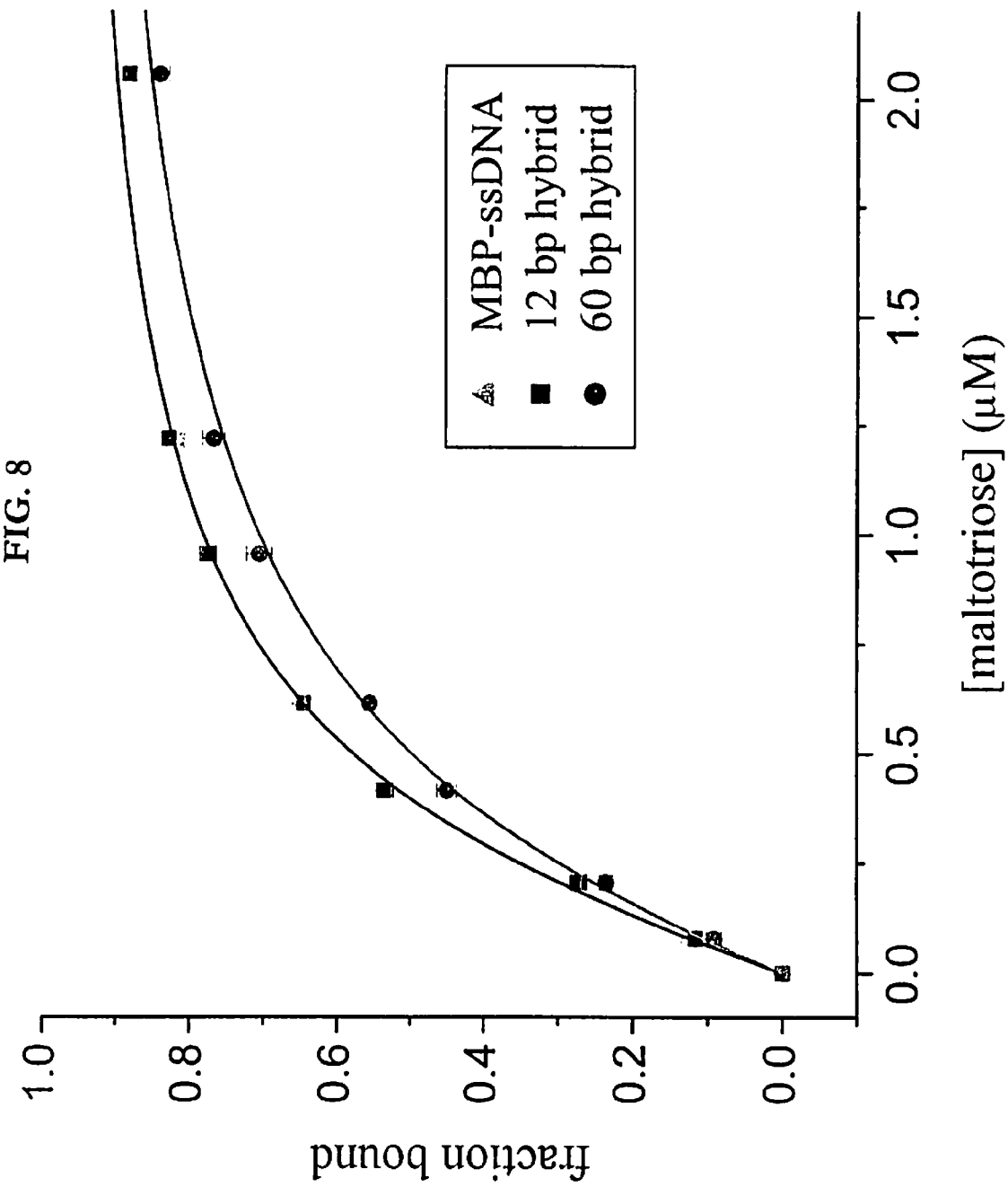
FIG. 8. Linear plot of the low concentration part of the titration curves of FIG. 2. All data are normalized so that the fraction bound is f=0 at zero concentration, and f=1 at saturating concentrations of substrate.

Varying the length of DNA hybridized to the chimera changes the mechanical tension on the protein. We performed experiments with hybrids of lengths L=0, 12, 20, 30, 40, 50, 60 bp. The corresponding maltotriose binding affinities are plotted in FIG. 3. To estimate the mechanical tension F for a given hybridization length L we constructed a mechanical model based on known parameters of DNA elasticity. In the model, the ds part of the DNA bends like a bow, while the ss ends act as (non-linear) springs (see FIG. 4 inset). The force exerted by the bow is calculated from the work per unit length required to bend it: $W/s=B/(2\ R^2)$, where s is the contour length of the bow, B the bending modulus, R the radius of curvature. For ds DNA, B≈200 pN×nm$^2$ (Bloomfield, V., Crothers, D., & Tinoco, I. *Nucleic Acids: structures, properties, and functions*, University Science Books, Sausalito, Calif. (2000)). The extension of the ss DNA "springs" is calculated from the mechanical equilibrium condition that the tension in the springs is the same as the force needed to bend the bow (FIG. 4 inset). For the force-extension characteristic of the "springs" we use the published force-extension curves for ss DNA (Dessinges, M. N. et al., Phys. Rev. Lett. 89, 248102 (2002); Singh-Zocchi, M., et al., Proc. Natl. Acad. Sci. USA 100, 7605-10 (2003)). The prediction of this model (which contains no adjustable parameters) is that substantial tension sets in for L≧36 (FIG. 4). Comparing FIG. 4 to the data of FIG. 3 supports the interpretation that the change in binding affinity is caused by the mechanical tension exerted by the DNA on the protein. Note that while the elastic energy stored in the DNA competes with the binding energy of hybridization, the total free energy of the system still favors hybridization (FIG. 4 inset). This conclusion is supported by experiments in which an intercalating fluorescent dye was used to monitor the degree of DNA hybridization on the chimera (FIG. 7).

Discussion

We have built an artificial allosteric control module into a protein. The principle is to use mechanical tension to influence the conformation of the protein. The tension is derived from the elasticity of another polymer coupled to the protein. Using a protein—DNA chimera we show that the tension can be controlled externally, in this case by the DNA sequence which is allowed to hybridize to the chimera. Based on the elastic properties of DNA, we estimate that we can obtain a significant tension on the protein, up to ~10 pN. Nonetheless, the effect on the binding affinity K is relatively small (~35% reduction). We believe that at present the observed effect is limited by the yield of complete chimeras in the samples. In addition, MBP binds the substrates also in the "open" conformation, only with a smaller K. A study where the conformation was forced permanently "open" by mutagenesis reports a ~50% reduction in binding constant. Finally, the labile protein-DNA connection on the Ni$^{2+}$ side probably limits the average tension. Indeed, our results with a Cys double mutant chimera, where the DNA is covalently attached at both ends (and the yield probably increased), show a larger (~60%) effect on K (inset of FIG. 2). To support our interpretation, we also show in FIG. 3 (continuous line) the result from the simplest thermodynamic model for K, which takes into account the above. Given a conformational motion of size s, an applied force F alters the free energy difference between the two states by F×s. We assume for the binding affinity:

$$K(F) = K_{closed} e^{-F \times s/kT} \quad (2)$$

for $F \leq F_0$ such that $K(F_0) = K_{open}$, and $K(F) = K_{open}$ for $F \geq F_0$. Here $K_{closed}$, $K_{open}$ are the binding affinities in the "closed" and "open" states: $K_{closed} \approx 5.3$ (µM)$^{-1}$ and $K_{open} \approx \frac{1}{2} K_{closed}$ (Marvin, J. and H. W. Hellinga, *Nat. Struct. Biol.* 8, 795-98 (2001)). With a yield p of correct chimeras, the values for F of FIG. 4, and the parameters above, we plot this model (for s=0.9 nm, p=0.6) as the continuous line in FIG. 3. The fit has one adjustable parameter (the yield p, or equivalently $K_{open}$).

To summarize the controls, we have shown, by hybridizing complementaries of different lengths L, that the threshold length to obtain an effect on K coincides with the estimated threshold where mechanical tension sets in (L≈34). The decrease in K for L>40 cannot be attributed simply to the presence of an extra DNA strand in close proximity to the protein, because a 60 mer with only 12 base complementarity (L=12), which therefore produces similar steric effects as the 60 mer true complementary, but no tension, does not affect K. Finally, if in the hybridized chimera we cut off one side of the protein-DNA connection (adding imidazole, which competes with the His-tag for binding to the $Ni^{2+}$), K returns to its original value (before hybridization).

This study opens a new approach to the control of protein function. It provides a new tool to study the relationship between protein function and conformation, because it allows external control of the conformation. In addition, such control of the catalytic rate of enzymes would open tremendous possibilities for applications. We envision amplified molecular probes, applied for instance to the detection of specific DNA sequences, as well as "smart drugs", which are turned on or off in the presence of certain transcription products.

Example 2

Allosteric Control Through Mechanical Tension

This example demonstrates insertion of a "molecular spring" on the enzyme Guanylate Kinase, to control the conformation of this protein. The stiffness of the spring can be varied externally, which allows exertion of a controlled mechanical tension between the two points on the protein's surface where the spring is attached. The example shows that by applying and releasing the tension, it is possible to reversibly turn the enzyme off and on.

Most enzymes in the cell are directly regulated by allosteric control. Unlike the control of gene expression, this mechanism provides fast response and is crucial in signaling pathways. In allosteric control, the signaling molecule binds to the enzyme at a site (A) distinct from the substrate's binding site (S). Separating A and S is an essential design feature because the substrate and the controlling molecule can then be unrelated chemically. Qualitatively, the local binding force at A produces a stress which is believed to propagate through the protein, modifying the conformation at S. The invention described herein allows the exertion of a controlled mechanical tension between any two chosen points on a protein's surface. This example, using the enzyme Guanylate Kinase, shows that by applying and releasing the tension, it is possible to control the enzymatic activity.

Figure 9:
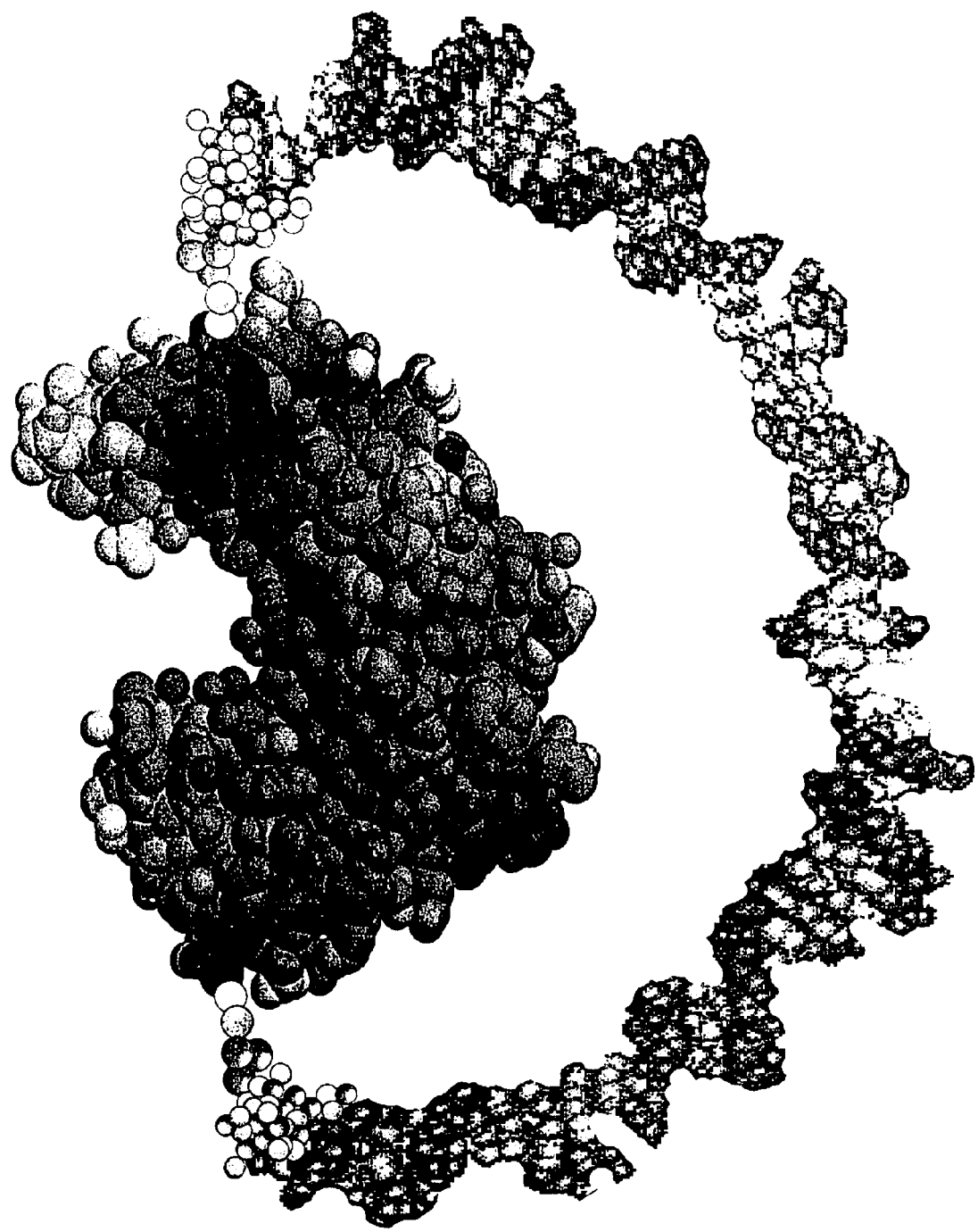
FIG. 9. The Protein-DNA chimera. The GK structure is PDB entry 1S4Q. The locations of the Cys mutations are shown in magenta. The distance between these two groups is 4.5 nm.

Guanylate Kinase (GK) is an essential enzyme which catalyzes the transfer of a phosphate from ATP to GMP; here we work with the 24 kDa protein from *Mycobacterium Tuberculosis*. The structure, shown in FIG. 9 [PDB entry 1S4Q], resembles a vice; when the substrates ATP and GMP bind inside the cavity, the "jaws" of the vice close through a ~1 nm conformational change. We reasoned that a mechanical tension favoring the "open" conformation of the enzyme would lower the binding affinity for the substrates, the rate of catalysis, or both. We accordingly constructed a chimera where the mechanical tension is provided by the elasticity of a second polymer coupled to the enzyme: in this realization, a DNA oligomer. To couple the DNA, we modified GK through site-directed mutagenesis (Thr 75→Cys; Arg 171→Cys) introducing a Cys residue on each of the two lobes of the molecule (FIG. 9). To those "chemical handles" the two amino-modified ends of a ss DNA 60 mer were covalently coupled through a cross-linker, resulting in the chimera shown in FIG. 9. By gel electrophoresis, the chimera can be easily distinguished from other species present in the samples, such as uncoupled GK, GK dimers (encouraged by the Cys modification), and DNA-coupled dimers. Partially coupled chimeras (where the DNA is attached by one end only) are however not distinguished on the gels. From the gels, the measurements below, and measurements on a different chimera which we report elsewhere, we estimate the yield p of correct chimeras in our samples to be somewhere between 50% and 70%, depending on the sample.

With this construction, we can exert a controlled mechanical tension between the two spots on the protein's surface where the DNA is attached. Namely, the ss DNA 60 mer of the chimera is a flexible polymer, and exerts no tension on the protein; however, it rigidifies upon hybridization with a complementary strand (the persistence length of ss DNA is $l_{ss} \approx 1$ nm or ~3 bases, while $l_{ds} \approx 50$ nm or ~150 bp). The rigid ds DNA has to bend in order to maintain the end-to-end distance imposed by the attachment points on the protein, therefore it exerts a mechanical stress on the protein, similar to the tension exerted by a bow on its string. This mechanical stress on the enzyme in solution can be controlled externally, by adding DNA partially or totally complementary to the DNA of the chimera. In this report, we show that we can thus modulate the enzyme's activity through the presence of a specific DNA sequence in solution. Furthermore, we obtain new insight into the architecture of this molecule by measuring how a mechanical stress applied between two specific residues far away from the active site alters the enzymatic activity.

Materials and Methods

Mutagenesis & Purification. The Rv1389c gene was amplified by PCR using *Mycobacterium tuberculosis* H37Rv genomic DNA as the template, forward primer: C CATATGGCTGTGAGCGTCGGCGAGGGACCGGACAC CAAGC (SEQ ID NO: 8), which introduced an NdeI site (underlined), and reverse primer: AAGCTTACCTCGTGG-TACACCCGGGGAGCCCGGTGCCGTTC (SEQ ID NO: 9), which introduced a HindIII site (underlined). The forward primer also inserted an alanine codon (GCT) immediately following the start codon to enhance protein expression (Looman et al., 1987), while the reverse primer introduced a thrombin recognition sequence to the C-terminus. The PCR product was cloned into pCRBluntII-TOPO (Invitrogen). Following sequence confirmation, the gene was subcloned into pET22b (Stratagene) which added a hexa-histidine tag to the expressed protein, following the thrombin recognition sequence.

The QuikChange Multi Site-Directed Mutagenesis Kit (Stratagene) was used to introduce the T75C and R171C mutations. The recombinant protein was expressed at approximately 10 mg/L/$OD_{600nm}$ in Rosetta(DE3) (Stratagene) *E. coli* in enriched buffered LB medium (10 g NaCl, 40 g tryptone, 20 g yeast extract per liter of medium, 5% glycerol, 10 mM MOPS, pH7.0). The mutagenesis was confirmed by sequencing. The his-tagged GK mutant was purified using a Superflow Ni-NTA® column (Qiagen). SDS-PAGE of the mutant showed a single, well defined band (purified protein was ≧99% pure). The protein was expressed at ~10 mg/L culture/OD (600 nm).

GK-DNA Complex conjugation. The 5'- and 3'-amino modified 60 base DNA oligomer (Operon) were conjugated to the NHS-ester end of the hetero-bifunctional cross-linker sulfo-SMCC (Pierce). The DNA and sulfo-SMCC were incubated together at 100 µM and 1.25 mM, respectively, for 80-90 minutes. Quenching of the NHS-ester ends of the free sulfo-SMCC was done by introducing an excess of tris buffer to the DNA and sulfo-SMCC solution. GK was reduced with dithiothreitol (DTT) (Sigma) in the presence of EDTA (Sigma) at 125 µM, 50 mM, and 1 mM respectively, for 30-40 minutes. Protein desalting spin columns (Pierce) were used to remove excess sulfo-SMCC and DTT. The un-reacted end of the sulfo-SMCC cross-linker is a maleimide group, which renders the DNA reactive to sulfhydryls, namely the Cys residues of GK. The solutions of GK and DNA were incubated together with a small amount of HCl to final concentrations of 65 µM, 50 µM, and 0.1 mM, respectively, for a period of 3-4 hours at 20-22 C, followed by an additional 18-24 hours at 4 C.

To remove unattached DNA from our GK-DNA mixture, the mixture was incubated with Ni-NTA agarose beads (Qiagen), chelating to the hexahistadine of GK. After washing, the GK-DNA conjugate was eluted from the beads using imidazole. To further purify the GK-DNA mixture from GK entities with free Cys, we used Sulfolink Coupling Gel (Pierce), which are agarose beads reactive towards sulfhydryl groups. The final GK-DNA complex was observed on a native polyacrylamide gel to have lower mobility compared to the GK mutant (the MW of GK is ~24.2 kDa and GK-DNA complex ~44 kDa which is hard to distinguish from GK-GK dimers having a MW of ~48 kDa).

Oligomer sequences. The sequence of the 60 mer used for the construction of the chimera was:

```
                                            (SEQ ID NO: 10)
5'-amino-GGCTCCCGATGCGGTCAGACCTGCTCTGCACTCC CCAGTACGTGCGGGCTGTCACTCGGT-amino
```

The ds hybrid was formed adding the complementary 60 mer in solution.

Enzyme Activity Assay. To measure kinase activity for GK, the Kinase-Glo (Promega) luminescence assay was used. The final concentrations of GK-DNA, GMP, ATP, and complementary DNA oligomers used in the assay were 1.1 µM, 6-350 µM, 1.25 µM, and 35 µM, respectively. The reaction time allotted for GK to catalyze phosphoryl transfer was 24 minutes, while the coupled subsequent reaction with the Kinase-Glo reaction buffer was 12 minutes. The luminescence measurements were performed on a Lumat LB 9507 luminometer.

Results

Figure 10:
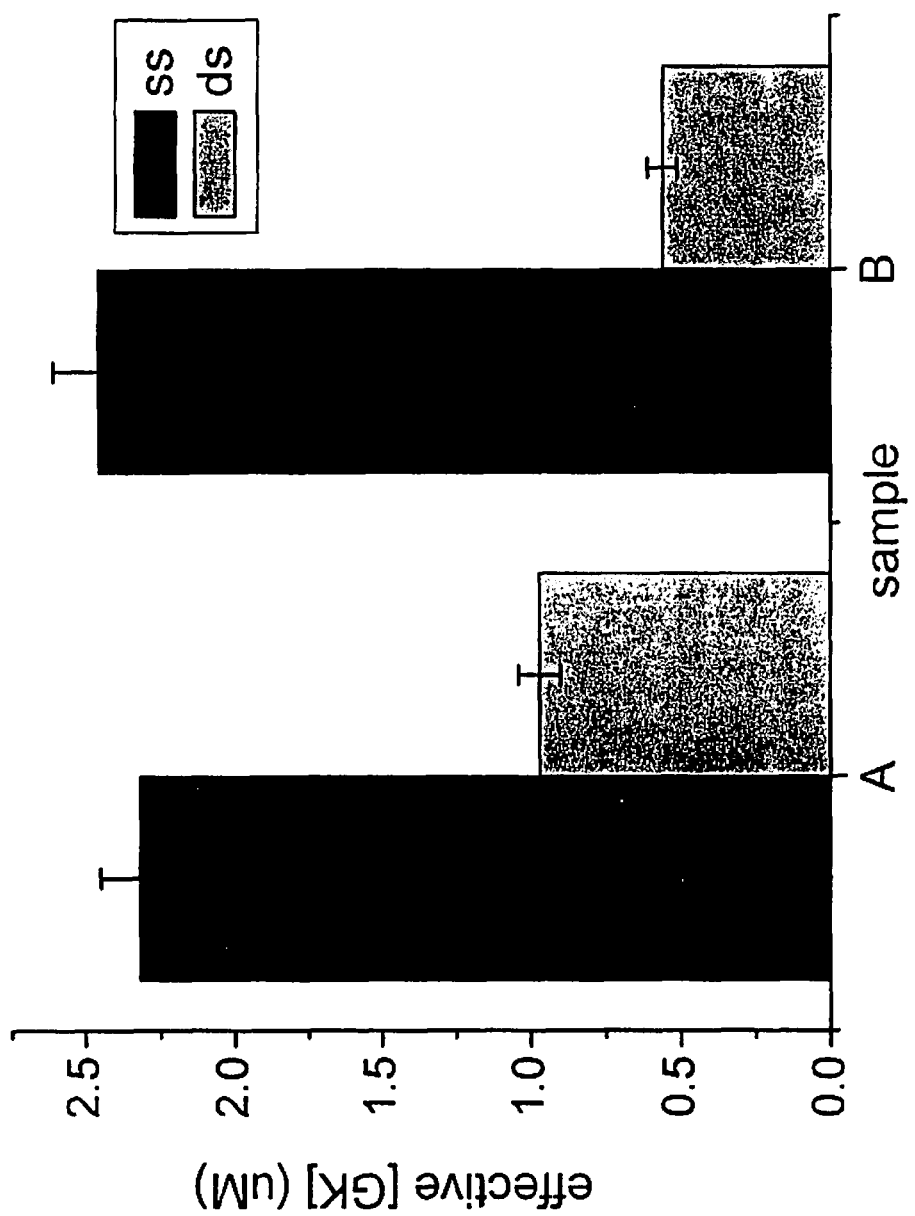
FIG. 10-11. Reduction in GK activity upon hybridization of the chimera. Data are the average of 4-5 experiments; the error bars are ±1 SD.
Figure 11:
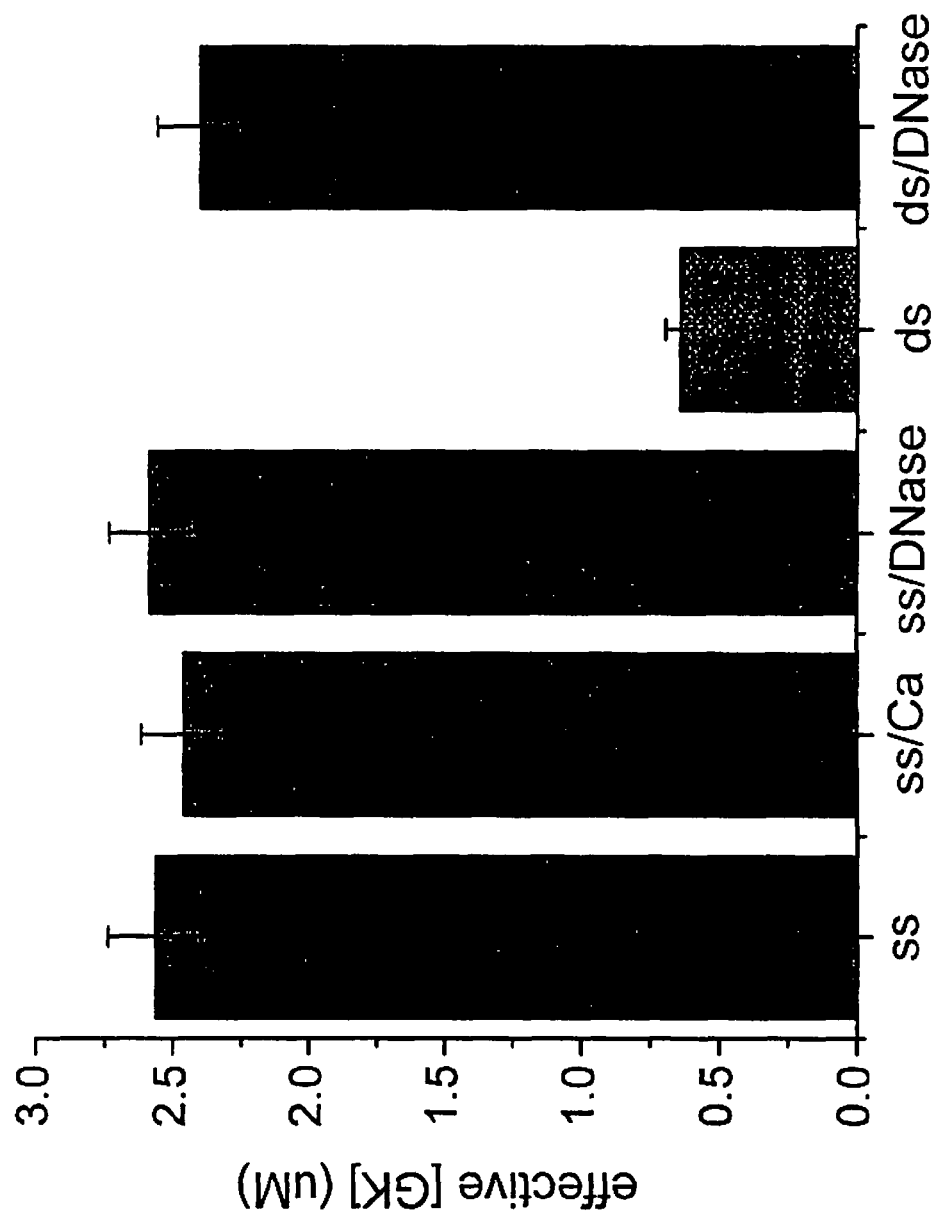

GK activity was measured using the Luciferase chemoluminescent assay, which monitors the conversion of ATP. A calibration curve was obtained to relate the measured luminescence (in RLU=Relative Light Units) to the concentration of 100% active GK; in the following, "effective [GK]" means RLU transformed into [GK] using the calibration curve. The enzyme activity of the mutant is about 20% lower than the wild type, and the activity of the ss chimera is indistinguishable from that of the mutant. FIG. 10 shows the reduction in kinase activity of the chimera upon introducing the complementary DNA 60 mer in solution, for different samples. The magnitude of the observed effect appears limited by the yield of correct chimeras. FIG. 11 shows that the reduction in activity is reversible: it disappears if the mechanical tension is released.

Figure 12:
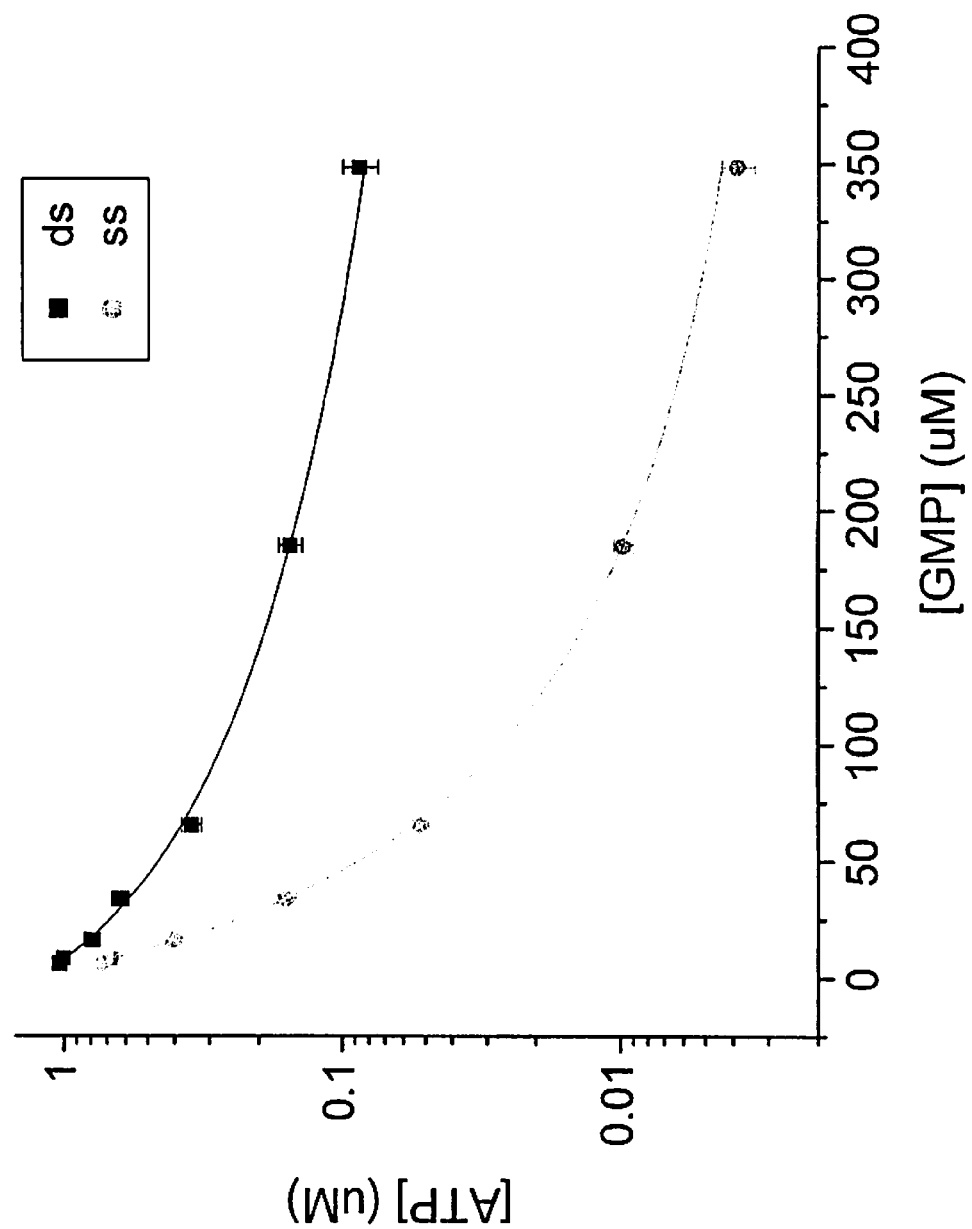
FIG. 12. The concentration of ATP remaining after a time $\tau$, $[A(\tau)]$, vs the initial GMP conc. $[G(0)]$, for the ss and ds chimera. $[A(\tau)]$ is a measure of the speed of the enzymatic reaction. Each experimental point represents the average of 4-6 measurements; error bars are ±1 SD. The ss data are fitted using eq. (6), the ds data using (9); the corresponding parameter values are listed in Table I.

Finally, the data in FIG. 12 give insight into the structure/function relation for this enzyme, as follows. Within the MM description, catalysis occurs in two steps:

$$E + S \underset{K_{-1}}{\overset{K_1}{\rightleftarrows}} ES \overset{K_2}{\rightarrow} R + E \quad (1)$$

(E, S, ES, R: enzyme, substrate, intermediate complex, product), characterized by the MM constant of the intermediate complex, $K_M=(K_{-1}+K_2)/K_1$, and the rate of the catalytic step, $K_2$. The speed of the reaction is:

$$\frac{d[R]}{dt} = P(\text{on})[E]_{tot} K_2 \quad (2)$$

where P(on) is the probability that the enzyme has a bound substrate:

$$P(\text{on}) = \frac{1}{K_M/[S] + 1} \quad (3)$$

With two substrates G (for GMP) and A (for ATP) the same approach (2), (3) leads to:

$$\frac{d[R]}{dt} = \frac{[E]_{tot} K_2}{(K_G/[G] + 1)(K_A/[A] + 1)} \quad (4)$$

We performed measurements not directly of d[R]/dt, but instead of the product formed after a time τ, for varying initial GMP concentrations [G(0)], at fixed initial ATP concentration [A(0)]. More precisely, in the experiments we measure the ATP concentration [A(τ)] remaining after the time τ. The data are shown in FIG. 12, for the ss and ds chimera. The assay conditions are such that $K_A/[A]>1$ and there is excess GMP over ATP; with the approximations $K_A/[A]+1 \approx K_A/[A]$, $[G] \approx \text{const.} = [G(0)]$, and since $d[R]/dt = -d[A]/dt$, (4) becomes:

$$-\frac{d[A]}{dt} = \frac{[E]_{tot} K_2/K_A}{1 + K_G/[G(0)]} [A] \quad (5)$$

with the solution:

$$[A(\tau)] = [A(0)] e^{-h\tau}, \quad (6)$$

$$h = \frac{[E]_{tot} K_2/K_A}{1 + K_G/[G(0)]}$$

We use (6) to fit the ss data in FIG. 12, and extract the parameters $(K_2/K_A)^{ss}$ and $K_G^{ss}$ (Table I). Under these assay conditions it is not possible to extract $K_2$ and $K_A$ separately. For the ds chimera, we must take into account that the experimental samples consist of a yield p (0<p<1) of correct chimera, plus a fraction of enzyme (1−p) which is functionally unmodified. Eq. (5) then becomes:

$$-\frac{d[A]}{dt} = (1-p)h^{ss}[A] + ph^{ds}[A] \quad (8)$$

where $$h^{ds} = \frac{[E]_{tot}(K_2/K_A)^{ds}}{K_G^{ds}/[G(0)] + 1},$$

$$h^{ss} = \frac{[E]_{tot}(K_2/K_A)^{ss}}{K_G^{ss}/[G(0)] + 1}$$

The solution is:

We use this form (with the ss parameters determined above) to fit the ds data in FIG. 12, obtaining the yield p≈0.7 and the ds parameters listed in Table I. The yield p≈0.7 is consistent with the evidence from the gels and the MBP measurements mentioned earlier, both of which indicate typical yields of our synthesis in the range 0.5<p<0.7. It is possible that p<0.7 in the present case; then the effect on the ds parameters (Table I) would be even bigger. The final result is that the mechanical tension, exerted between Thr 75 and Arg 171 (FIG. 9), i.e. between helices α2 and α6 (FIG. 13A), increases the MM constant for the substrate GMP, $K_G$, at least 10-fold, while the ratio ($K_2/K_A$) decreases by less than a factor 2. A big effect on $K_G$, a smaller effect on $K_2$ and/or $K_A$.

TABLE I

The values of the parameters extracted from the fits in FIG. 12.

| | |
|---|---|
| $K_G^{ss}$ (μM) | 82 ± 2 |
| $K_G^{ds}$ (μM) | 788 ± 13 |
| $(K_2/K_A)^{ss}$ | 0.25 ± 0.02 |
| $(K_2/K_A)^{ds}$ | 0.17 ± 0.01 |

Discussion

Figure 13A:
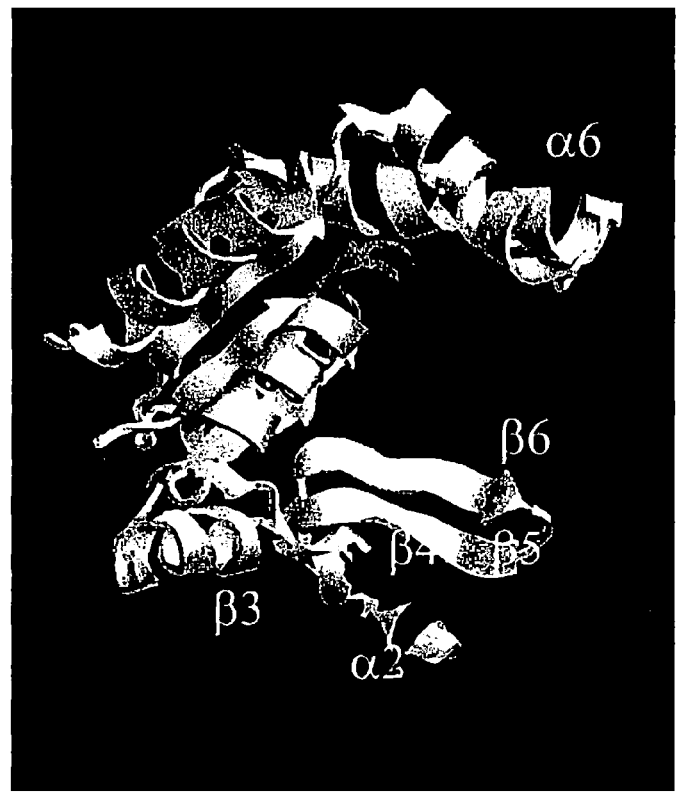
FIG. 13A-B. The conformational change between the "open" (FIG. 13A: ligand-free) and "closed" (FIG. 13B) conformation of GK, from the PDB structures 1EX6 and 1GKY. While these structures are of the yeast protein, the structure of the TB protein used in this study is essentially identical. The structural location of the Cys mutations, where the mechanical stress is applied, is shown in red. The GMP binding site is colored blue, the ATP binding site green. Inspection of the structures suggests that the applied mechanical stress, between helices $\alpha 2$ and $\alpha 6$, favors the open conformation, and probably deforms the GMP binding site more than the ATP one. This correlates with the measured change in the binding constants for the two substrates upon applying the mechanical stress (see Table I).
Figure 13B:

The static picture is that the applied mechanical stress significantly deforms ("opens") the GMP binding pocket, without disrupting too much the ATP binding site (disruption of the ATP binding site would increase $K_A$, while $K_2$ would decrease or stay the same, so the ratio ($K_2/K_A$) would decrease). Future independent measurements of $K_A$ will settle this question, but for the moment we note that this correlates with the known structures of the open (ligand-free) conformation of GK [5 and PDB entry 1EX6] vs the closed conformation (with GMP bound [5 and PDB entry 1GKY], or both substrates bound [9 and PDB entry 1LVG]). FIG. 13A-B shows that the whole domain consisting of helix α2 and strands β3, β4, β5, β6 swings to "closed" (FIG. 13B) upon GMP binding [5], with less drastic changes for the ATP binding domain. Our mechanical tension, applied between α2 and α6, presumably reverses this conformational change and deforms the GMP binding site. Such structural deformations could be investigated experimentally by FRET measurements, and computationally by MD simulations (J. Ma, P. B. Sigler, Z. Xu and M. Karplus, *J. Mol. Biol.* 302, 303, 2000).

The dynamic picture (reviewed in D. Kern and E. R. P. Zuiderweg, *Curr. Opin. Struct. Biol.* 13, 748 (2003)) could be quite different. A dynamical mechanism for allostery has been suggested whereby binding of the regulatory molecule alters the spectrum of long-wavelength elastic excitations of the protein; this translates into an entropic contribution to the free energy of substrate binding (A. Cooper and D. T. Dryden, *Eur. Biophys. J.* 11, 103 (1984); S. Jusuf, P. J. Loll and P. H. Axelsen, *J. Am. Chem. Soc.* 125, 3988 (2003); R. J. Hawkins and T. C. B. McLeish, *Phys. Rev. Lett.* 93, 098104 (2004)). Our molecular spring affects both the statics and the dynamics, and in fact it could be used to test specific predictions of the Cooper & Dryden dynamical mechanism. Similarly, even small, single-domain proteins exist in a statistical ensemble of conformational substates (H. Frauenfelder, F. Parak, and R. Young, *Annu. Rev. Biophys. Biophys. Chem.* 17, 451 (1988)), which can be functionally distinct. In this language, allostery arises because ligand binding alters the energy landscape and thus the statistical weights of the substates (H. Frauenfelder et al., *Proc. Natl. Acad. Sci. USA* 98, 2370 (2001); I. Luque, S. A. Leavitt and E. Freire, *Annu. Rev. Biophys. Biomol. Struct.* 31, 235 (2002)). The "molecular spring" offers a practical implementation for this mechanism, vindicating the view that any protein is—or can be—allosterically controlled. Clearly through this method we can ask new questions about structure/function relation.

It seems likely that, given a large enough mechanical tension, the enzyme could be completely shut off, because eventually the protein will unfold. The tension in the present construct can be estimated from the bending modulus of DNA (see Example 1 above); we find that the DNA stores an elastic energy of order W ~25 $kT_{room}$ and provides a force of order F ~10 pN. This is an upper bound, as it does not take into account force-limiting effects such as, for instance, bubble formation in the DNA.

Our approach differs from previous work on artificial allostery, where metal ion binding sites were engineered into a protein to control a conformational change (Marvin, J. S, and Helling a, H. W., *Proc. Natl. Acad. Sci. USA* 98, 4955 (2001); H. Liu et al., *Nat. Mater.* 1, 173 (2002)); it is also conceptually different from recent, innovative work where external control is achieved by blocking the active site (Shimoboji, T. et al, *Proc. Natl. Acad. Sci. USA* 99, 16592-96 (2002)) Important features of our "spring-loaded" molecules are the externally controlled mechanical tension, which can be continuously modulated, and the possibility of applying the tension between any two chosen points on the protein's surface. The present study suggests that allostery can be explained or mimicked in terms of mechanical tension originating from local binding forces. Perhaps allosteric proteins are similar to our chimera, with part of the polypeptide chain playing the role of the DNA, but all integrated in the protein structure. For the enzyme GK, we have measured how a specific mechanical stress affects substrate binding. Further studies for varying ATP concentration and different application points for the stress will reveal new details. Finally, we foresee exciting biotechnology applications for these chimeras, as amplified molecular probes and "smart" drugs.

Example 3

Mimicking cAMP Dependent Allosteric Control of Protein Kinase A through Mechanical Tension This example describes the activation of an enzyme complex by mechanical tension. Protein kinase A, a tetrameric enzyme that, in the cell, is allosterically controlled by cAMP, has been modified by the insertion of a "molecular spring" on the regulatory subunit. This allows the exertion of a controlled mechanical tension between the two points on the protein's surface where the spring is attached. We show that upon applying the tension we can activate the enzyme, with efficiency comparable to the activation by its natural regulatory molecule, cAMP.

Many experimental results on allostery can be understood in terms of a thermodynamic model first introduced by Monod, Changeux, Wyman and later modified in different ways, where the general mechanism is that regulatory molecules and substrates bind to different conformations of the protein with different binding constants. In contrast, here we are concerned with building a microscopic understanding of allostery, from "microscopic" experimental measurements. We ask what stresses, and applied where on the protein's surface, result in what modulation of the function. For the first time, we present experiments where the stress is controlled: we control the points of application of the stress, and we can externally vary the magnitude of the stress semi-continuously. We measure the response of the protein in terms of its function (enzymatic activity). We do not yet measure the response in terms of conformation.

Our experimental system is the Protein Kinase A (PKA; also known as cAMP-dependent Protein Kinase: cAPK), a tetramer composed of two regulatory and two catalytic subunits. PKA is allosterically regulated by cAMP; it is in fact the primary receptor for cAMP in eukaryotic cells, playing a crucial role in signaling pathways and numerous metabolic processes. Stringent regulation of PKA is necessary to maintain normal cellular activity; its failure is connected to pathologies such as proliferating cancer cells. PKA consists of a regulatory subunit (RS) dimer and two catalytic subunits (CS) which form a catalytically inept tetrameric holoenzyme complex. The RS binds to the CS through a surface of contact which includes the catalytic site, which is thus not accessible in this state.

Upon cAMP binding, the RS undergo a conformational change which causes the CS to dissociate from the complex, activating catalysis. With the catalytic site freed of the RS, the CS catalyzes the phosphoryl transfer from an adenosine triphosphate (ATP) to a Ser/Thr residue on target proteins. Thus, the enzymatic activity of PKA is regulated by cAMP. In this case, positive control is in fact achieved by removing a negative control element.

Our aim in the present work is to obtain allosteric control of PKA by directly applying a controllable stress between two chosen points on the surface of the regulatory subunit. We choose the application points of the stress on two elements of the protein's secondary structure which are known to move with respect to each other in the cAMP-induced conformational change; our applied stress goes in the direction of favoring this motion. We find that this mechanical stress, which is in fact applied far away from the cAMP binding site, is at least as effective as cAMP in turning on kinase activity, presumably by causing the dissociation of the catalytic subunits. The mechanical stress is exerted by a "molecular spring" made of a short piece of DNA, which we chemically couple to the regulatory subunit by specifically attaching the ends of the DNA to Cysteine residues introduced at specific locations by site directed mutagenesis. The stiffness of the DNA spring can be varied externally by hybridization with complementary DNA of varying lengths, providing external control over the mechanical stress.

Compared to the above examples relating to Maltose Binding Protein and Guanylate Kinase, where we achieved allosteric inhibition through mechanical tension, here we demonstrate allosteric activation. The multimeric PKA is also a considerably more complex system compared to the monomeric proteins of our previous work; taken together, the present and previous studies suggest that our experimental approach can be applied to virtually any protein.

Materials and Methods

To obtain the dissociation constant of RS towards cAMP, fluorescence measurements were performed on a Photon Technology Instruments fluorimeter, in 3 mL cuvettes, at 20±2° C. The excitation and emission wavelengths were $\lambda_{ex}=281$ nm and $\lambda_{em}=341$ nm. The concentration of the SG-chimera was approximately ~50 nM in phosphate buffered saline (PBS).

The fraction of proteins with bound cAMP is given by $$f = \frac{[M]}{[M]+K_d} \quad (8)$$

Results and Analysis

Figure 14:
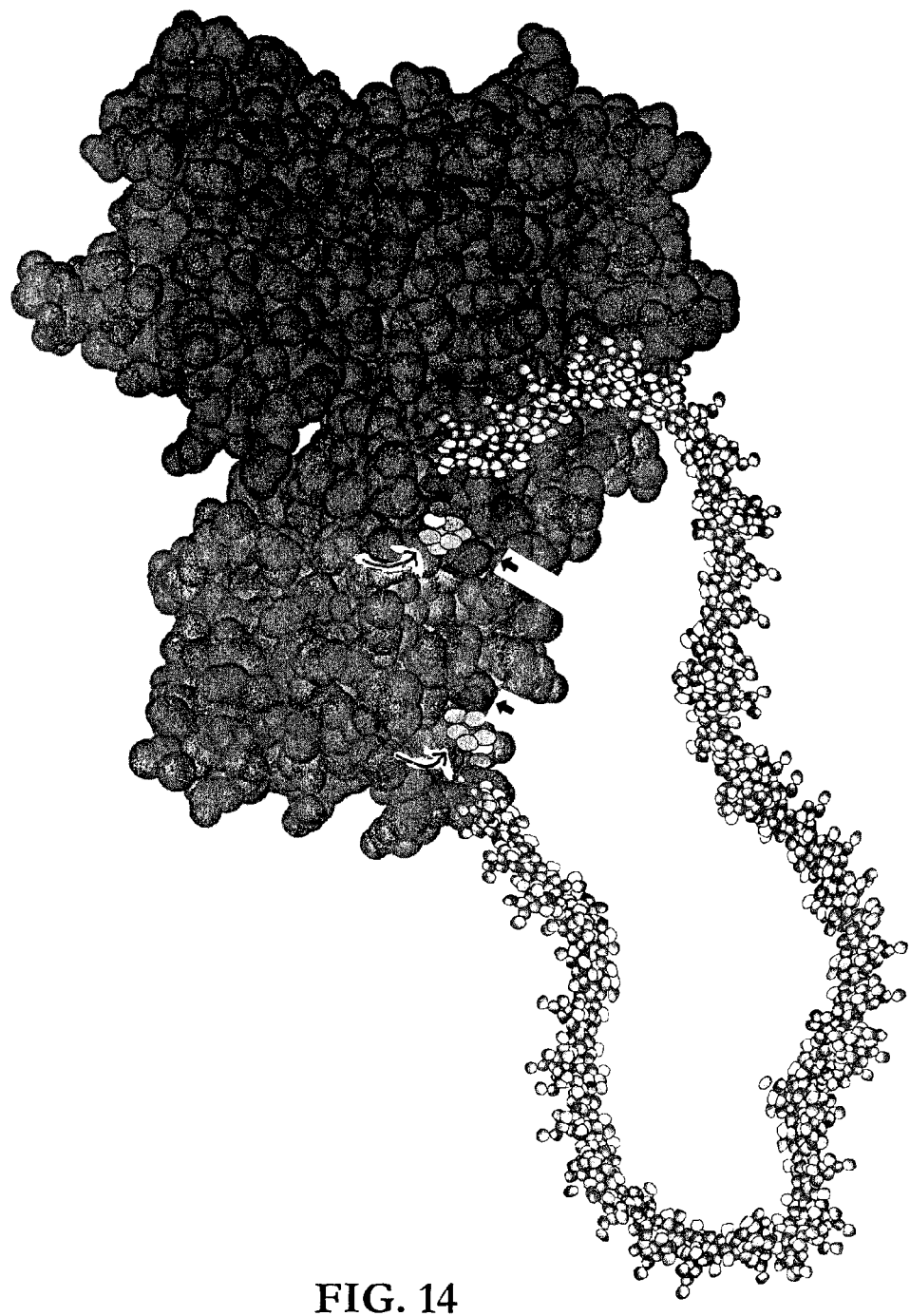
FIG. 14. Cartoon of the protein-DNA chimera (as a dimer). The PKA holoenzyme complex is from the PDB structure 1U7E. It consists of the regulatory subunit (right portion of dimer) bound to the catalytic subunit (left). The DNA molecular spring (loop) is 60 bases long. Native PKA is a tetramer of two regulatory and two catalytic subunits; the crystal structure shown is a deletion mutant (D(91-244)) of the regulatory subunit which does not allow for two regulatory subunits to be linked. The locations of the Cys mutations (spring attachment points) on the regulatory subunit are indicated with straight arrows. The distance between these two sites is approximately 2 nm. Note that the attachment sites (curved arrows) of the ss DNA are sterically distant from the contact surface between the two subunits.
Figure 15A:
FIG. 15a-15b. Highlights of the conformational change of the regulatory subunit induced by cAMP binding (which is the natural allosteric control mechanism of PKA).
Figure 15B:
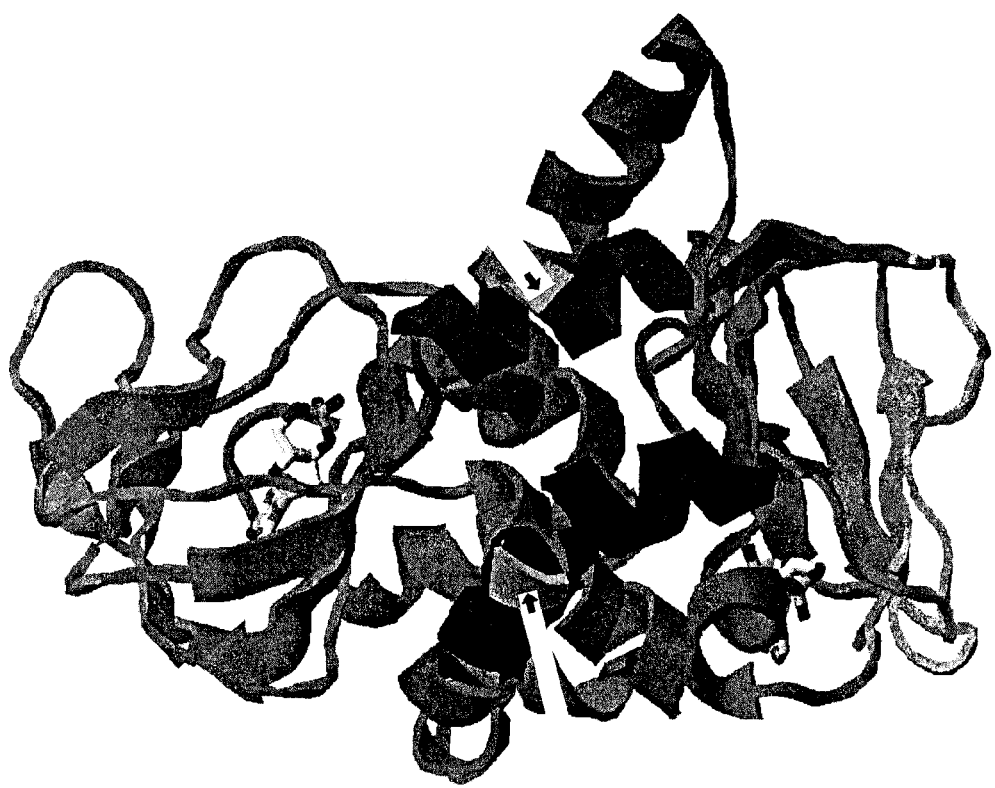

The conformational changes associated with the cAMP-dependent allostery of PKA have been studied in detail in the lab of Susan Taylor at UCSD. Here we work with the same recombinant form of PKA as in those studies: the RS (which is a RIα isomer) is from *mus musculus* and the CS from *bos taurus*. In fact, for the mutagenesis we used plasmids kindly provided by Prof. Taylor. The structure of the CS+RS holoenzyme is shown in FIG. 14 [Protein Data Bank (PDB) entry 1U7E]. Comparison of the CS-bound state (PKA holoenzyme) against the dissociated (cAMP-bound) state reveals a significant conformational change in the RS; particularly in the drastic movement of the αA:A (α-helix of domain A of RIα) with respect to αC:A as shown in FIG. 15 [PDB entry 1U7E and 1RGS, respectively]. αA:A (blue in FIG. 15b) and αC:A (red in FIG. 15b) are nearly parallel in the CS-bound conformation (FIG. 15a); where upon binding cAMP the αC:A of RIα rotates away from αA:A (FIG. 15b). It could be argued that the αC:A and αA:A orientations for the CS-bound structure are influenced by the fact that the crystal structure is based on a deletion mutant Δ(91-244). However, in a separate experiment using amide hydrogen/deuterium exchange-Mass spectroscopy (DXMS) the Taylor group showed that these two regions undergo an enormous change in deuteration between cAMP bound and CS-bound states. We accordingly assumed that the relative displacement of the two α-helices depicted in FIG. 15 represents an important part of the cAMP-induced conformational change which causes the subunits to dissociate, and this provided the rationale for the choice of our spring attachment points.

The "molecular spring" is made of a short (60 bases) piece of DNA, and exploits the property that the persistence length of ds DNA ($l_{ds}\approx 50$ nm or 150 bp) is much larger than the persistence length of ss DNA ($l_{ss}\approx 1$ nm or 3 bases), therefore at lengthscales in between $l_{ss}$ and $l_{ds}$, ds DNA is much stiffer than ss DNA. The idea of using this property to construct a controllable spring has been exploited before in several clever configurations, notably in the molecular beacons, and in an experiment where an inhibitor is removed from an enzyme (thus activating catalysis) by literally pulling it off by means of such a spring. In our case, we covalently attach the ends of a ss DNA 60 mer to two Cys residues which have been introduced by mutagenesis on the RS at the positions marked on the two α-helices in FIG. 15. Coupling of the DNA to the RIα was done via a heterobifunctional crosslinker, covalently bonding the site-directed mutations (Ser 145→Cys; Gly 235→Cys) of the RS to the 5'/3'-amino modified ends of the ssDNA 60 mer. A cartoon of the resulting RIα-DNA holoenzyme chimera is shown in FIG. 14. Referring to FIG. 14, this DNA in the ss form is very flexible (as its length is about 20 times $l_{ss}$), so it exerts essentially no mechanical tension on the attachment points. To be precise, the average tension exerted by the DNA on the protein, which is always in the direction of the line joining the attachment points, is a small entropic compression for the ss form (i.e. a small force tending to push the attachment points towards each other). The magnitude of this small compression force can be estimated from the Flory theory of polymer elasticity, and it is <1 pN in the present case. In the following, we call this construction of RS+ss DNA the "ss chimera"; when viewing cartoons such as FIG. 14, it is well to remember that the DNA is unstructured, i.e. is fluctuating between all conformations compatible with the fixed ends (so for instance the protein can "jump the rope" etc.). The cartoon of FIG. 14 also implicitly conveys the assumption that the ss DNA does not significantly adsorb on the surface of the protein. In the measurements and controls described below, we do not find evidence for a significant non-specific protein-DNA interaction of this sort in this system. However, this is a question which, for different proteins, must be considered case by case.

Now if the complementary DNA strand is introduced in solution, it will hybridize to the DNA strand of the chimera; the resulting ds 60 mer can be thought of roughly as a semiflexible rod (having a contour length of about ⅓ $l_{as}$), which has to bend due to the constraint of the fixed end-to-end distance (for a fixed protein conformation; FIG. 16). The ds DNA therefore exerts a large average force on the attachment points on the protein, directed along the line joining the attachment points and tending to separate them (i.e. an extension). One can think of the ds DNA as a strung bow, where the "string" connecting the ends of the bow is therefore under tension. This mechanical tension can be estimated from the bending modulus B of ds DNA, and it is large. To give a rough idea of the numbers, in a purely mechanical picture, the elastic energy E of a rod of length L bent through a radius of curvature R is:

$$\frac{E}{L} = \frac{1}{2}\frac{B}{R^2} \quad (1)$$

where B is the bending modulus. For ds DNA the bending modulus is related to the persistence length through:

$$B \approx kT\, l_{ds} \quad (2)$$

which gives B≈200 pN×nm². The description expressed by (1) and (2) is appropriate if L<$l_{ds}$ (which is our case), and R is not too small compared to $l_{ds}$ (which is not quite our case). Here it is just a simple way to estimate an upper bound for the elastic energies and forces. Putting in the numbers (L≈20 nm; R≈3.5 nm), we find: E≈40 $kT_{room}$. The force on the attachment points can also be calculated from (1), and one obtains forces of order F ~10 pN for our situation. The elastic energies and forces which can be obtained from this "molecular spring" are "large", in the sense that they are expected to affect the conformation of the protein substantially.

In summary, the configuration of FIG. 14 allows us to exert a controlled mechanical tension between residues, up to values which will strongly affect the conformation of the subunit. In the ss chimera, there is essentially no tension. Introducing the complementary DNA in solution, we go to a situation (FIG. 16) where there is a large mechanical tension, the force being directed along the line joining the residues, and tending to pull them apart. This mechanical stress tends to favor the displacement of the α-helices shown in FIG. 15, which is part of the cAMP-induced conformational change of the RS which results in dissociation of the CS. With the chimera, the mechanical tension can be varied semi-continuously by hybridizing complementary sequences of varying lengths to the DNA of the chimera.

In the experiments, we reconstitute the holoenzyme with the chimera as the regulatory subunit, and measure kinase activity of this holoenzyme, the holoenzyme+complementary DNA, the holoenzyme+cAMP, the holoenzyme+ complementary DNA+cAMP, and various controls. Kinase activity is measured using the Luciferase assay, which monitors the disappearance of ATP. The choice of parameters (i.e. concentrations) in the assay reflects a compromise: relatively low ATP concentration is desirable to maximize the sensitivity of the assay, but relatively high ATP concentration promotes association of the holoenzyme and thus a larger dynamic range in the measurements.

The mutant RS showed a negligible difference in holoenzyme formation and >80% of the inhibitory effects of the wild type RS, while the chimera showed roughly a 20% decrease in associating with the CS to form the holoenzyme. We present data for two different initial ATP concentrations.

In FIG. 17 we present the results from two different batches (independent synthesis) of the chimera, in the form of "kinase activity" A, quantified by the amount of ATP remaining in the enzymatic reaction mixture (containing the combination specified on the abscissa, ATP, and a synthetic peptide substrate for PKA, see Methods) a fixed time after adding the substrate. In FIG. 17a, the total concentration of chimera enzyme (holoenzyme+dissociated enzyme) is the same for all samples, by construction. We have normalized the activity A(Chi+cAMP) to 1, so all other activities are relative to this. The first result is that the holoenzyme chimera is still a competent allosteric enzyme. Starting from the holoenzyme chimera, addition of cAMP—the natural activator—increases kinase activity by a factor ~3. The second result is that adding the complementary DNA, i.e. turning on the mechanical tension, also activates the enzyme: kinase activity increases by a factor ~2. The same data could be presented differently, by subtracting from all columns the "background activity" of the sample (Chi); then we would say that the complementary DNA is about half as effective in activating the enzyme as cAMP. This difference is most likely due to the finite yield of correctly constructed chimeras in the samples (i.e. chimeras with both ends of the DNA attached at the correct sites), as we argue below. When the yield is taken into account, we find that the complementary DNA, i.e. the mechanical tension, is at least as effective as cAMP in activating the enzyme. Thus the main result is that an opportunely placed mechanical tension, in this case applied between the two residues in FIG. 15, can, as far as function is concerned, mimic the natural allosteric mechanism, in this case activation by cAMP.

FIG. 17b shows an independent set of measurements on a different chimera synthesis batch, where we also compare with the cAMP-induced activation of the holoenzyme constructed with the double Cys mutant (but no DNA attached: denoted by SG on the abscissa in the Figure). In FIG. 17b the total enzyme concentration is the same by construction within all the "Chi" columns, and within the two "SG" columns, but it is not necessarily identical between the "Chi" and the "SG" columns, the samples coming from different purification histories. The total enzyme concentration is approximately the same based on the Bradford assay, however this leaves room for differences. Therefore the data in FIG. 17b are presented with both the columns (SG+CS+cAMP) and (Chi+cAMP) normalized to 1, and what is to be compared is the dynamic range of allosteric control for the SG case (compare the first two columns) and for the Chi case (compare the last four columns) We see that in the case of the mutant (SG), cAMP activation increases kinase activity by a factor of approximately 3, while for the chimera cAMP activation increases activity by a factor of about 2. These data are consistent (within error bars) with the measurements of FIG. 17a, although the latter show a somewhat larger dynamic range of allosteric control for the chimera (close to a factor 3). The important conclusion from the data is that the presence of the ss DNA on the chimera probably interferes somewhat with the cAMP-induced allosteric control, but not much: mutant (without DNA) and chimera have almost the same dynamic range (a factor 2-3 increase in kinase activity with cAMP). Our interpretation is that cAMP is probably close to 100% efficient in dissociating the catalytic subunits, both in the case of the mutant and the chimera, but for the chimera the presence of the ss DNA interferes a little bit with the formation of the holoenzyme complex, leading to a somewhat higher "background" activity for the chimera holoenzyme. Our choice of normalization for the data in FIG. 17b (i.e. R(SGCS+cAMP)=1; R(Chi+cAMP)=1, where R stands for measured rate) reflects this interpretation. Finally, the complementary DNA in FIG. 17b has an apparent effect which is about half that of cAMP, but, as before, we believe this merely reflects a yield of correct chimeras in the samples of order 50%.

We have performed a control measurement (FIG. 17a column "Chi+loop") where a DNA 60 mer which is only partially complementary to the DNA of the chimera is hybridized to the chimera; this "loop" complement leaves large single-stranded bubbles between double-stranded segments. The bubbles act as hinges which release the tension, resulting in a configuration which is very close to the ds chimera as far as the possibility of the DNA interacting with the protein's surface is concerned, but with no (or a much reduced) mechanical tension. The purpose is to demonstrate that the mere presence of a second DNA oligomer in close proximity to the ss chimera does not by itself cause activation of PKA, supporting our view that it is the mechanical tension which is responsible for the observed activation of the chimera upon hybridization with the true complementary.

In our previous work [GK] we have obtained (indirect) measurements of the yield of correct chimeras obtained from our coupling and purifying procedure; this yield lies somewhere between 0.5 and 0.7 depending on the sample (while these measurements refer to a different protein, the chemistry for coupling the DNA to the Cys was the same, so we expect, barring exceptional cases, similar yield with other proteins also). In order to take into account a finite yield in the present case, we use the following simple model.

The rate of consumption of ATP is given by:

$$\frac{d}{dt}[ATP] = -r[ATP] \quad (1)$$

where r is the catalytic activity. Thus:

$$[ATP](t)=[ATP](0)e^{-rt} \quad (2)$$

where [ATP](t) is the concentration of ATP at time t.

In the experiments we measure the ratio between the initial and final concentration of ATP after a fixed time $\tau$, i.e. we obtain the catalytic activity from:

$$r = \frac{1}{\tau}\ln\left\{\frac{[ATP](0)}{[ATP](\tau)}\right\} \quad (3)$$

The best resolution in the measurements is obtained by choosing $\tau \approx 1/r$. In the following, we call A(ss), A(ds), A(ss, cAMP) etc. the enzymatic activities of the ss chimera, ds chimera, ss chimera+cAMP, etc. We describe the increase in activity due to allosteric activation caused by either the complementary DNA or the cAMP by introducing parameters $\gamma_{DNA}$, $\gamma_{cAMP}$ as follows:

$$A(ds) = \gamma_{DNA} A(ss)$$

$$A(ss, cAMP) = \gamma_{cAMP} A(ss) \quad (5)$$

This Ansatz is correct if all measurements are done at a fixed total (=undissociated+dissociated) concentration of PKA. In general, the more fundamental description would be in terms of the dissociation constant for the holoenzyme, which is different in the presence or absence of the allosteric activators. The factors $\gamma$ above are functions of the two dissociation constants (with and without activator), and the total conc. of PKA. The functional form can be determined easily, and in principle the values of the two dissociation constants can be determined by using this functional form to fit titration curves of the activities vs. the total conc. of PKA.

For the moment, we consider instead that in the experimental samples there is a finite fraction ("yield") p (0<p<1) of "correct" chimeras, i.e. chimeras with the DNA correctly attached at both ends. In fact, we know from the synthesis and purification procedure (see Methods) that $p \leq p_{max} = 0.7$. For the measured kinase activity r (operationally defined above) we can then write:

$$r(ds) = p\,\gamma_{DNA} A(ss) + (1-p) A(ss)$$

$$r(ss, cAMP) = \gamma_{cAMP} A(ss)$$

$$r(ds, cAMP) = p\max\{\gamma_{DNA}, \gamma_{cAMP}\} A(ss) + (1-p)\gamma_{cAMP} A(ss) \quad (6)$$

The term $\max\{\gamma_{DNA}, \gamma_{cAMP}\}$ means we take the parameter with the higher value. These equations express the fact that cAMP affects all the holoenzymes in the sample, while the complementary DNA affects only the fraction p of holoenzymes which have the DNA correctly "installed". Further, A(ss)≡r(ss), and there is an assumption in the 3d equation, that the effect of the two different activators is "not cumulative". A sufficient condition for this is for instance that at least one of the activators leads to nearly 100% dissociation of the holoenzyme. This assumption is consistent with the experimental data on the DNA activator (FIG. 17a-b, which show that r(ds, cAMP)=r(ss, cAMP). The corresponding data on the cumulative effect of cAMP show however r(ds, cAMP)>r (ds) because of the yield p<1.

Now there are two cases: $\gamma_{DNA} > \gamma_{cAMP}$ or $\gamma_{DNA} < \gamma_{cAMP}$. If we assume $\gamma_{DNA} \geq \gamma_{cAMP}$ we can extract all three parameters (p, $\gamma_{DNA}$, $\gamma_{cAMP}$) from the data. If we assume instead $\gamma_{DNA} < \gamma_{cAMP}$ we can obtain only lower and upper bounds for $\gamma_{DNA}$ and p from the data. We assume first $\gamma_{DNA} \geq \gamma_{cAMP}$. Solving the system of linear equations (6) for p, $\gamma_{DNA}$, $\gamma_{cAMP}$ in the case $\max\{\gamma_{DNA}, \gamma_{cAMP}\} = \gamma_{DNA}$ we obtain:

$$1 - p = \frac{r(ds, cAMP) - r(ds)}{r(ss, cAMP) - r(ss)} \quad (7)$$

$$\gamma_{cAMP} = \frac{r(ss, cAMP)}{r(ss)}$$

$$\gamma_{DNA} = \frac{1}{p}\frac{r(ds)}{r(ss)} - \frac{1-p}{p}$$

Using the data we obtain:

$$p = 0.39 \pm 0.07;\ \gamma_{DNA} = 2.7 \pm 0.4;\ \gamma_{cAMP} = 2.6 \pm 0.3 \quad (8)$$

i.e. $\gamma_{DNA} = \gamma_{cAMP}$ within experimental error, consistent with the initial assumption. This extracted yield is within the range of our estimates from previous work [GK] and is consistent with the evidence on the native protein gels, where RS-DNA chimeras can be distinguished from other species present in the samples, such as uncoupled RS, RS dimers (encouraged by Cys mutations), and DNA coupled dimers. Partially coupled chimeras (where the DNA is attached by only one end) are, unfortunately, not distinguished from the correct chimera on the gels, so the gels give again only an upper bound for the yield.

If we assume instead max $\{\gamma_{DNA}, \gamma_{cAMP}\} = \gamma_{DNA}$ in (6), then the equations are consistent if r(ds, cAMP)=r(ss, cAMP), which is the case in the experiments, and either of the last two equations determines $\gamma_{cAMP}$, while the first eq. gives a relation between p and $\gamma_{DNA}$:

$$\gamma_{cAMP} = \frac{r(ss, cAMP)}{r(ss)} \quad (9)$$

$$p(\gamma_{DNA} - 1) = \frac{r(ds)}{r(ss)} - 1$$

Since we know that $0.4 < p < p_{max} = 0.7$ (the lower limit coming from the treatment of the opposite case $\gamma_{DNA} > \gamma_{cAMP}$, the upper limit from the preparation methods), we can use the data and eqs. (9) to obtain the limits:

$$\gamma_{cAMP} = 2.3; \quad 1.6 < \gamma_{DNA} < 2.3 \quad (10)$$

In summary, the data show that the mechanical tension is, if not just as efficient, then almost as efficient as cAMP in activating PKA.

Discussion

We have built an artificial allosteric control module into the enzyme PKA. The basic principle is to use mechanical tension to influence the conformation of the regulatory subunit, which in turn controls the dissociation of the catalytic subunit from the complex and thus the activity of the protein. The mechanical tension is derived from the externally controllable elasticity of another polymer coupled to the protein; a short piece of DNA in this case. We estimate that the molecular spring can provide forces and elastic energies which can significantly alter the protein's conformation.

The raw data show an increase in the activity of PKA induced by stiffening the molecular spring of more than 50%, but this is limited by the yield of the synthesis and purification of the chimeras. We believe that a sample of 100% chimeras would show an efficiency of activation by the stiffening the spring close to that induced by cAMP. Further, this second allosteric module does not interfere substantially with the natural (cAMP-dependent) one.

Some interference is however present. Indeed, it would be strange if the presence of a 30 kD piece of DNA attached to the RS (in the ss chimera) did not interfere at all with the association of the holoenzyme. FIG. 17b shows that, assuming the DNA on the chimera does not interfere with cAMP binding (which we prove below by cAMP titration experiments), and if we accordingly normalize both the (SGCS+cAMP) and the (Chi+cAMP) columns to 1, then the mutant is more competent than the chimera in associating into the holoenzyme complex (since R(SG)<R(Chi)), but not dramatically so.

Another question is whether the ss chimera and the ds chimera, which is under tension, have the same binding affinity for cAMP, and whether this is the same as the binding affinity of the SG. We have performed cAMP titration measurements of the ss and ds chimera, and of the SG, obtained exploiting the Tryptophan fluorescence quenching associated with cAMP binding. The result is that the binding affinity for cAMP is the same in the three cases, within error, and consistent with previous measurements by the Taylor group.

The previous example shows how, through mechanical tension, one can turn off the activity of an enzyme; here we achieve, on the contrary, activation of the enzyme PKA. Demonstrating allosteric control of PKA using our "mechanical" approach represents a significant step with respect to our previous work on Guanylate Kinase (GK), also because the multimeric PKA enzyme is considerably more complex than the monomeric GK. Taken together, our results argue that the concept of controlling protein conformation by mechanical stress is general, applicable to virtually any protein or protein complex. One could speculate what interesting observations this approach might lead to when applied to complex molecular machinery such as the ribosome. Even molecular motors could be studied from a new angle, by imposing stresses within the motor, rather than between the motor and the tracks.

Our approach differs from previous work on artificial allostery, where metal ion binding sites were engineered into a protein to control a conformational change; it is also conceptually different from recent, innovative work where inhibition is achieved by blocking the active site, and activation is achieved by mechanically removing an inhibitor. The strength of our approach is that it allows to investigate the very mechanism of allostery, i.e. how a mechanical stress applied at specific sites is transported through the complex structure of the protein to affect the static or dynamic conformation at distant sites. It is a general approach which is not restricted to blocking an active site, or removing an inhibitor from an active site.

The conformational change of the RS of PKA underlying the natural allostery mechanisms is complex: it involves many more rearrangements than the displacement of the $\alpha$-helix in FIG. 15. With this experiment, we show that, by pulling on the attachment points shown in FIG. 15, the effect is the same as that induced by cAMP: dissociation of the catalytic subunit from the complex (with similar efficiency).

This is one of a series of experiments by which we aim to build a microscopic understanding of allostery, by probing which application points for the stress result in allosteric behavior similar to the natural one (elicited by cAMP in the case of PKA), and which do not. This approach, where the mechanical stress is controlled, provides a more incisive research tool for understanding allostery than mutagenesis studies alone.

We measure the effect of the stress on the protein's function, but not on the structure. Major structural changes could be detected in a relatively simple way by CD spectroscopy. Local information on structural changes can in principle be obtained by fluorescence energy transfer (FRET) methods, both from ensemble and single-molecule measurements. The main difficulty here is that the corresponding experimental system needs 4 specific labels on the same protein: 2 attachments for the spring, and 2 attachments for the FRET labels; to be specific, the attachment chemistry must be different for the two sets. In the end, the most practical way of obtaining structural information could be through NMR; also, crystallizing at least some chimeras. In addition, obtaining the structure from X-ray scattering, while probably difficult, cannot be ruled out.

The principle of the invention is manifestly general, and we have so far demonstrated it experimentally on 3 different proteins. This shows that we can make an allosteric control module for virtually any protein. This approach also provides for the construction of new amplified molecular probes, and actively controlled ("smart") drugs.

Throughout this application, various publications are referenced (articles, patents, patent applications etc.). The disclosures of these publications are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

The invention claimed is:

1. A method of altering the conformation of a polypeptide having a known three-dimensional structure, wherein the polypeptide comprises two domains and a binding cleft between the two domains, or an enzyme, the method comprising:
(a) covalently attaching a first end of a synthetic single stranded polynucleotide to a first portion of the polypeptide;
(b) covalently attaching a second end of the single stranded polynucleotide to a second portion of the polypeptide; and
(c) altering the mechanical tension of the single stranded polynucleotide by hybridizing the single stranded polynucleotide to a complementary polynucleotide;
thereby altering the conformation of the polypeptide.

2. The method of claim 1, wherein the polynucleotide is DNA, or RNA.

3. The method of claim 1, wherein the polynucleotide is from about 10 to about 100 bases in length.

4. The method of claim 1, wherein the polypeptide is a kinase or a sugar-binding protein and the alteration of the conformation of the polypeptide lowers the binding affinity of the polypeptide for a substrate or other molecule bound by the polypeptide relative to the binding affinity for the substrate or other molecule prior to the alteration of the conformation of the polypeptide.

5. The method of claim 1, wherein the polypeptide is a kinase or a sugar-binding protein and the alteration of the conformation of the polypeptide increases the binding affinity of the polypeptide for a substrate or other molecule bound by the polypeptide relative to the binding affinity for the substrate or other molecule prior to the alteration of the conformation of the polypeptide.

6. The method of claim 1, wherein the alteration of the mechanical tension of the polypeptide is reversibly controlled by varying access of the polypeptide to the single stranded polynucleotide.

7. A composition comprising a polypeptide coupled to a synthetic single stranded polynucleotide, wherein a first end of the polynucleotide is covalently attached to a first portion of the polypeptide and a second end of the polynucleotide is covalently attached to a second portion of the polypeptide, wherein the polypeptide comprises (i) a sugar-binding protein comprising two domains and a binding cleft between the two domains, or (ii) a kinase, and wherein the single stranded polynucleotide is selected so that:
(a) upon contact with a chemical signal, the polynucleotide exerts an alteration of mechanical tension on the polypeptide of about 1 to about 10 pN; and
(b) the alteration of mechanical tension on the polypeptide effects an alteration of the binding affinity for a substrate or other molecule bound by the polypeptide and/or catalytic rate of the polypeptide.

8. The composition of claim 7, wherein the chemical signal is a complementary polynucleotide.

9. The composition of claim 7, wherein the polypeptide is a kinase.

10. The composition of claim 9, wherein the alteration of the mechanical tension on the enzyme effects an alteration of the catalytic rate of the kinase.

11. The composition of claim 7, wherein the alteration of the binding affinity for a substrate or other molecule bound by the polypeptide and/or catalytic rate effects production of a detectable signal.

12. The composition of claim 11, wherein the detectable signal is mediated by a fluorescent agent, a chemiluminescent agent or a chromophore.

13. A method of detecting the presence of a target molecule in a sample comprising:
  (a) contacting the sample with a composition according to claim 11, wherein the target molecule is the chemical signal; and
  (b) detecting the presence of the detectable signal, whereby presence of the detectable signal is indicative of the presence of the target molecule.

14. The method of claim 1, wherein the polypeptide comprises an enzyme.

15. The method of claim 14, wherein the enzyme catalyzes a reaction leading to the production of a fluorescent or chemoluminescent molecule, or a chromophore.

16. The method of claim 14, wherein the enzyme is a kinase.

17. The method of claim 1, wherein the polypeptide comprises two domains and a binding cleft between the two domains.

* * * * *